United States Patent
Doughty et al.

(10) Patent No.: US 7,344,498 B1
(45) Date of Patent: Mar. 18, 2008

(54) OPTICAL MEASUREMENT METHOD OF SKIN STRAIN DURING SHAVING

(75) Inventors: Darrell Gene Doughty, Cincinnati, OH (US); Pamela Joan Zupkosky, Westford, MA (US)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 11/656,619

(22) Filed: Jan. 23, 2007

(51) Int. Cl.
*A61B 5/00* (2006.01)
*A61B 5/103* (2006.01)
*A61B 5/117* (2006.01)

(52) U.S. Cl. ..................... 600/306; 600/587
(58) Field of Classification Search ............. 600/306, 600/557, 552, 553, 587, 595, 300
See application file for complete search history.

(56) References Cited

U.S. PATENT DOCUMENTS

| | | | |
|---|---|---|---|
| 1,118,014 A | 11/1914 | Jennings | |
| 1,658,356 A | 2/1928 | Schaaff | |
| 2,190,008 A | 2/1940 | Beitel, Jr. | |
| 2,328,700 A | 9/1943 | Wiltberger | |
| 2,464,001 A | 3/1949 | Shepard | |
| 2,937,567 A | 5/1960 | Hardy et al. | |
| 3,801,188 A | 4/1974 | Hunt et al. | |
| 4,169,169 A | 9/1979 | Kitabatake | |
| 4,848,898 A | 7/1989 | Massof | |
| 5,054,502 A * | 10/1991 | Courage | 600/587 |
| 5,278,776 A * | 1/1994 | Fisher et al. | 600/587 |
| 5,379,235 A * | 1/1995 | Fisher et al. | 600/587 |
| 5,446,548 A | 8/1995 | Gerig et al. | |
| 5,578,353 A | 11/1996 | Drew, III | |
| 5,678,546 A * | 10/1997 | Truppe | 600/426 |
| 5,801,809 A | 9/1998 | Husain | |
| 6,042,881 A | 3/2000 | Ewan | |
| 6,161,554 A | 12/2000 | Dunlap-Harris | |
| 6,324,419 B1 * | 11/2001 | Guzelsu et al. | 600/476 |
| 6,341,831 B1 | 1/2002 | Weber et al. | |
| 6,352,502 B1 * | 3/2002 | Chaiken et al. | 600/473 |
| 6,457,585 B1 | 10/2002 | Huffer et al. | |

(Continued)

FOREIGN PATENT DOCUMENTS

DE 196 13 978 10/1997

(Continued)

OTHER PUBLICATIONS

Tyson, Schmidt and Galanulis, "Optical Deformation & Strain Measurement in Biomechanics", Biophotonics, pp. 1-7 Sep. 2003.

(Continued)

*Primary Examiner*—Charles A. Marmor, II
*Assistant Examiner*—Navin Natnithithadha
(74) *Attorney, Agent, or Firm*—Kevin C. Johnson

(57) ABSTRACT

A contact-less, optical method of measuring strain on a skin surface of a human test subject during shaving. Digital cameras record the deflection of a pattern applied to the skin as a series of digital images. Comparison of the deflected skin position under applied forces compared to an undeflected reference condition permits calculation of the strain in the skin. Strains in the skin are averaged over several positions of the razor blade unit during a stroke. Objective comparisons can be made between razors based on the strain data.

20 Claims, 21 Drawing Sheets

U.S. PATENT DOCUMENTS

| | | |
|---|---|---|
| 6,596,118 B1 | 7/2003 | Bailey |
| 6,681,133 B2 * | 1/2004 | Chaiken et al. ............. 600/473 |
| 6,699,569 B2 | 3/2004 | Lipper |
| 6,793,999 B2 | 9/2004 | Wittmeyer, Jr. |
| 7,011,401 B2 | 3/2006 | Markey, III |
| 2005/0105051 A1 | 5/2005 | Jones et al. |
| 2005/0195363 A1 | 9/2005 | Sato |
| 2005/0213039 A1 | 9/2005 | Ohashi et al. |

FOREIGN PATENT DOCUMENTS

| | | |
|---|---|---|
| DE | 198 44 256 | 3/2000 |
| DE | 102 41 752 | 3/2004 |
| DE | 10 2004 046 752 | 4/2006 |

OTHER PUBLICATIONS

Tyson, Schmidt and Galanulis, "Biomechanics Deformation and Strain Measurements with 3D Image Correlation Photogrammetry", Experimental Techniques vol. 26, No. 5, Sep./Oct. 2002 pp. 39-42 (ProQuest Science Journals).

ARAMIS User Manual v5.4.1, submitted in color, pp. 1-148 (pubd. by manufacturer GOM mbH Mittelweg 7-8, 38106 Braunschweig Germany 2005).

"Ishihara Eye Test Charts" description from website of Kappa Medical, Inc. http://www.kappamedical.com/ishihara_eye_test_charts.htm visited Jul 7, 2006, 3 color pgs.

* cited by examiner

FIG. 17: Translation and strain of a line element
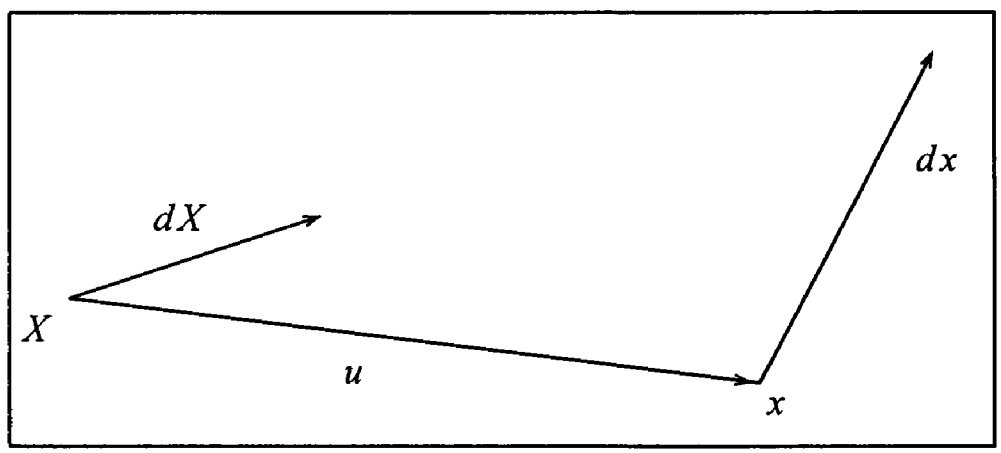

FIG. 18: Geometrical model of central projection
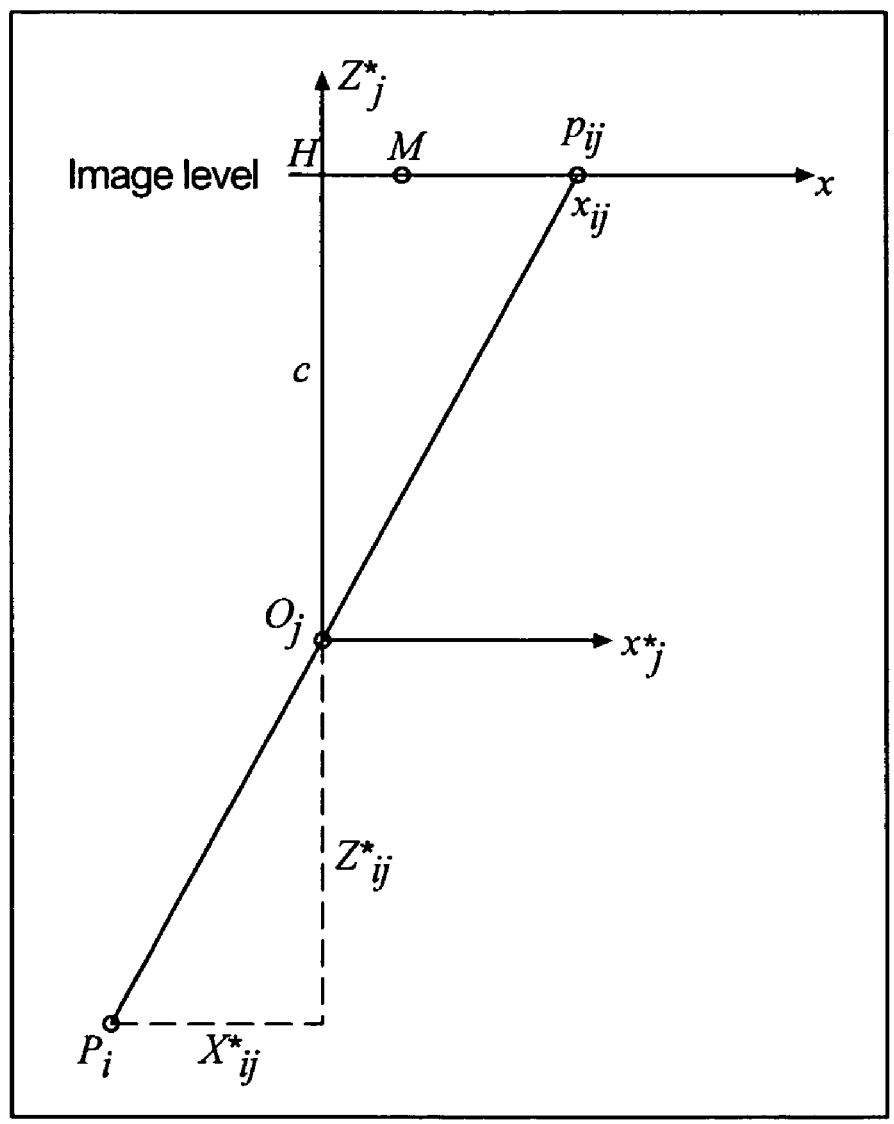

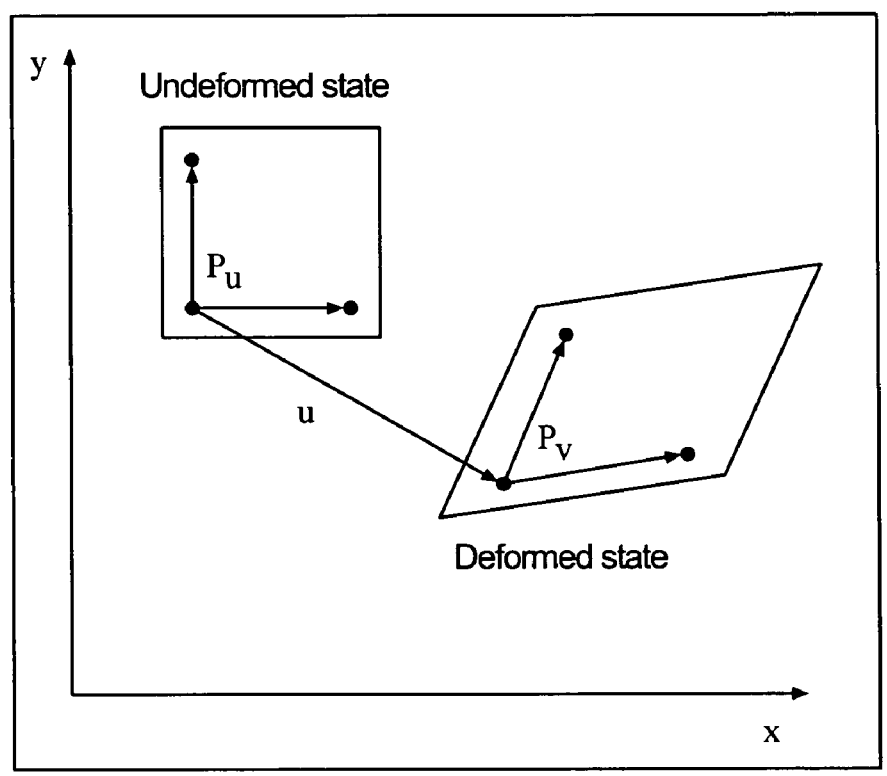
FIG. 19: Analytical calculation of the deformation gradient tensor

FIG. 20: 3 x 3 neighborhood for strain calculation
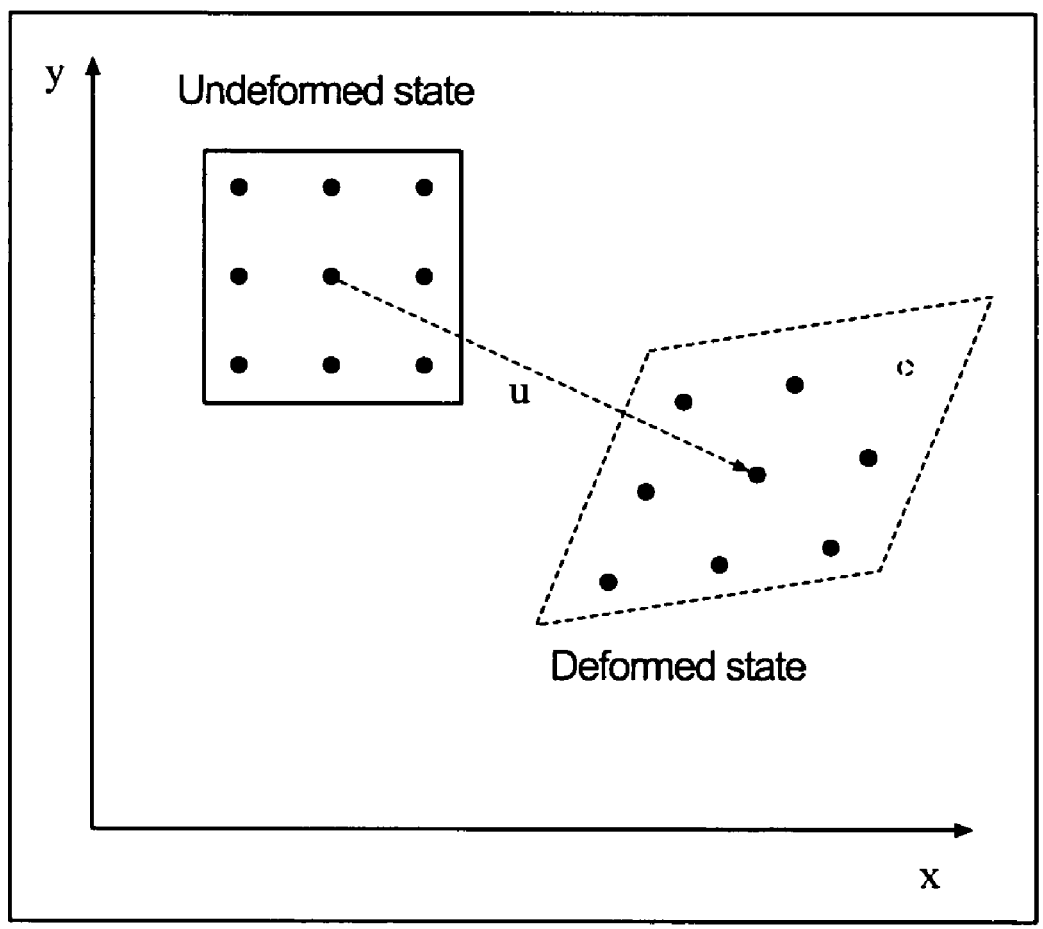

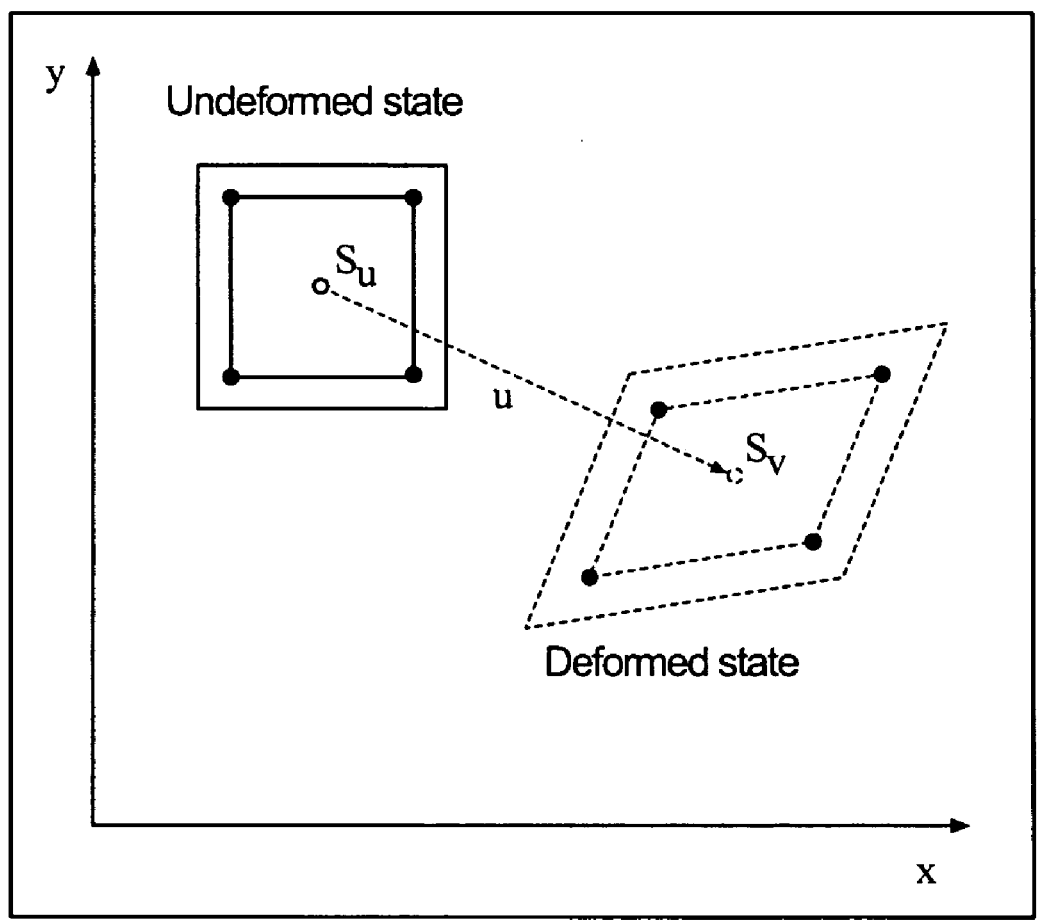
FIG. 21: Neighborhood for a four-sided facet

FIG. 22: Four-sided facet with adjacent points
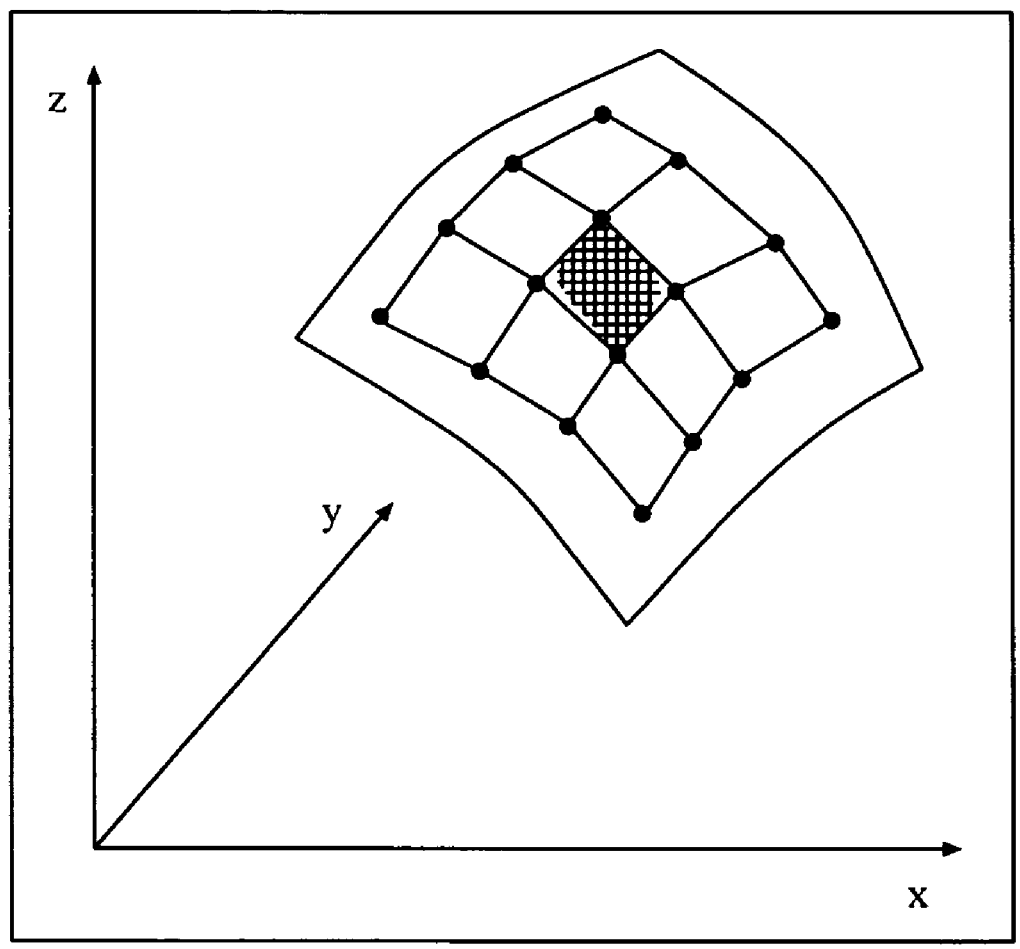

OPTICAL MEASUREMENT METHOD OF SKIN STRAIN DURING SHAVING

FIELD OF THE INVENTION

The present invention relates to a non-contact method of measuring strain on an external skin surface of a person while the person is performing an action on the skin, such as shaving the skin.

BACKGROUND OF THE INVENTION

It has been known to use three dimensional (3D) image correlation photogrammetry as a full-field, non-contact optical inspection technique to analyze strain in machine parts and dissected tissue specimens. This technique is described for example in the literature by Tyson, J., Schmidt, T. Galanulis, K. "Optical Deformation & Strain Measurement in Biomechanics", in *Biophotonics*, September 2003, pages 1 to 7; and by Tyson, J., Schmidt, T., Galanulis, K., "Biomechanics Deformation and Strain measurements with 3D Image Correlation Photogrammetry", Experimental Techniques, Vol. 26, No. 5, pages 39-42, September/October 2002 (ProQuest Science Journals). This literature describes strain testing of dissected bone, knee tendon, and ligament specimens that have been removed from a cadaver and ruptured under tensile testing, of a heart of a vivisectioned frog, and of flexed artificial muscle specimens. Known industrial applications of this measurement system are for aerospace or machine parts. These biologic specimen and industrial applications involve objects held in a fixture during testing. Measurement systems of this type are in wide use in the aerospace industry and in public universities (including the Universities of Maine, Wichita State in Kans., and Akron in Ohio), with at least 300 of them in use in Europe and 40 in the United States. For example, the United States space agency NASA used this technique to make measurements of the full Space Shuttle wing leading edge (NASA Johnson Space Flight Center & Southwest Research) as well as for External Fuel Tank (ET) foam impacts (Lockheed Martin Manned Space Systems). This technique allows for non-contact determination of 3D coordinates and 3D displacements, 3D speeds and accelerations, and plane strain tensor and plane strain rate.

An example of a commercially widely available 3D image correlation photogrammetry digital camera system is the system made by the company GOM mbh marketed under the trade designation ARAMIS system.

The preparation of the specimen with a pattern is described in the above "Biomechanics Deformation" and "Optical Deformation" articles, or alternatively in the "ARAMIS User Manual", at pages 26-27, published by the GOM company (2005), as a high-contrast stochastic (random) pattern consisting of a sprayed-on dye penetrant developer (such as white) overlaid with a sprayed-on black spray (e.g. a matte black spray or graphite spray), for example by lightly pressing the spray button on commercially available cans of spray paint. It is also known to apply the pattern by means of a pen or a stencil/spray technique. It is known that smooth specimen surfaces are preferred. The pattern can be a regular or random pattern. It is known that it is preferred for the pattern to avoid large areas of constant brightness such as wide lines. It is known that it is preferred to avoid a shiny pattern and to prefer a pattern with a matte or dull surface.

Temporary tattoos made from dyes or inks approved for use in food or cosmetics are known for novelty purposes, as body adornment, or to mark a person's hand as having paid an admission price. These typically involve a recognized, ordered arrangement of graphic elements, or text, as known for example in U.S. Pat. Nos. 5,578,353 (Drew, III); 7,011,401 (Markey, III); 6,161,554 (Dunlap-Harris); and 6,457,585 (Huffer et al.). Some such tattoos are transferred to the person by the tattoo's having a pressure-sensitive adhesive layer. Other such tattoos are printed on a paper substrate with water soluble ink, and the paper placed in contact with the skin in the presence of moisture and the ink is transferred to the skin.

Dot patterns are known in eye color-blindness tests such as the Ishihara color chart (named after its designer Dr. Shinobu Ishihara, a professor at the University of Tokyo, who published his test in 1917) which uses colored plates having a background of dots in the middle of which is a recognizable regular pattern, differentiated by color, usually in the shape of an Arabic number or English letter, see also U.S. Pat. No. 2,937,567 (Hardy) and U.S. Pat. Appln. 2005/0213039 (Ohashi). These eye charts are usually printed on heavy stock and carefully preserved against soiling so as to be used by eye care professionals to diagnose patients.

There remains a need to determine strain fields on the skin surface of a living human interacting with a product used on the skin in a manner comfortable to the test subject person.

There remains a further need to quickly and/or conveniently apply a removable pattern to a human test subject.

SUMMARY OF THE INVENTION

It is an object of the invention to provide a method of measuring strain on the skin of a living person while the person uses a shaving apparatus such as a dry shaver or a wet razor to shave hairs on the skin. A wet razor, also referred to as a safety razor, is an instrument having a sharp razor blade, such as in a cartridge disposed on a handle, in conjunction with a shave preparation product such as water typically applied to the skin in combination with a shaving cream, gel or lotion, to shave hairs on the skin.

It is a further object of the invention to provide a method of measuring skin strain on the external skin of a person while applying a force to the skin, such as by a finger or blunt probe object dragged along a portion of skin to which a cosmeceutical product, such as a lotion, cream or emollient, has been applied.

In one aspect, the invention features a method of measuring a parameter indicative of deformation of skin surface of a living person resulting from a force applied to the skin surface during the test. The skin of the person being tested is first provided with a pattern and then is imaged by two digital cameras. The cameras then capture reference image data of the undeformed or reference position of the patterned skin surface. While applying a force to the skin, the cameras capture second image data indicative of the deformed position of the patterned skin surface. The reference data and stressed or deformed condition data is stored and processed to determine movement of the patterned skin surface relative its reference position. At least one parameter indicative of this movement ("deformed state") of the patterned skin surface relative its reference position ("undeformed state") is determined. Preferably that parameter is a numerically quantifiable parameter. More preferably that parameter is a strain. The parameter determined can be a strain tensor or a strain rate. The parameter determined can be major strain or minor strain. The parameter determined can alternatively be positional coordinates, displacements, speed, or acceleration of the skin.

In certain implementations of the method: The force applied to the skin can be from shaving, or by a finger or blunt probe drawn across the skin. A performance characteristic of a razor can be quantified such as the strain produced in the skin surface during use. Comparisons can be made between razors or a prototype evaluated during development. An efficacy of a cream or lotion applied to the skin can be evaluated.

Advantageously in certain implementations of the method, the quantity of the movement, such as an amount of strain during shaving with a razor, can be determined over several different measurement areas of the shaving stroke. An average strain can be determined for each measurement area. This advantageously allows quantifying performance of a razor over a representative range of its intended use. An overall average strain quantity can be determined from the several measurement areas.

Advantages of the present invention include that the optical measurement system is not invasive to the user, it does not touch the test person's skin not interfere with normal motion using a product that applies force to the skin. Another advantage of the inventive method is that allows the test person to freely move his or her body and act in a normal, unconstrained manner, thus more realistic replicating conditions of normal use, since translational or so-called rigid body motions are subtracted out and do not distort the measurements. The test subject can shave himself or herself, or draw the finger (or blunt probe) across the skin, or another a test administrator can apply the force to the test subject.

The pattern applied to the skin can be a regular pattern or a random pattern. A random pattern is also referred to as a stochastic pattern. The pattern can be applied as a multitude of "dots" to the test person's skin.

In another aspect, the invention features a prepared pattern that is easily applied to the skin of a test subject and is also removable after the optical measurements. A removable tattoo is provided with a substrate and a pattern having a plurality of indicia randomly distributed to form a pattern density of between about 40% and about 60%. In advantageous embodiments the indicia is in the form of dots.

In another aspect, a tattoo to pattern the skin for optical measurements is provided having a substrate and a random pattern (45) having a plurality of distributed dots. The dots are made with an ink or dye that is substantially water insoluble but is substantially soluble in an alcohol. The substrate can be moisture permeable, e.g. to alcohol.

In advantageous embodiments the individual elements that make up the indicia or dots have two different sizes. In further embodiments there are three, or more, different sizes present in the pattern.

In further advantageous embodiments, the removable tattoo has a pattern density of about 50%. In other, presently yet more preferred embodiments, the pattern density is about 42.5%.

In further embodiments the tattoo is transferable to the skin by wetting with an alcohol. The substrate can be a paper, such as paper commonly referred to as blotting paper or cigarette paper. The tattoo can be printed with an oil-based ink or dye.

The tattoo is preferably made convenient by being devoid of a cover layer formed above the pattern on the tattoo, thus obviating the need to peel off such a layer before applying it to the skin. The tattoo is also made convenient and economical to manufacture by being devoid of an adhesive layer.

Further embodiments are disclosed in the dependent claims attached hereto.

The present invention and its advantages will be better understood by referring, by way of example, to the following detailed description and the attached Figures.

BRIEF DESCRIPTION OF THE DRAWINGS

FIG. 17 shows a reference diagram depicting translation and strain of a line element;

FIG. 18 shows a reference diagram depicting a geometrical model of central projection;

FIG. 19 shows a reference diagram depicting an analytical calculation of the deformation gradient tensor;

FIG. 20 shows a reference diagram depicting a 3×3 neighborhood for strain calculation;

FIG. 21 shows a reference diagram depicting a neighborhood for a four-sided facet; and FIG. 22 shows a reference diagram depicting a four-sided facet with adjacent points.

DETAILED DESCRIPTION OF PREFERRED EMBODIMENTS OF THE INVENTION

The Imaging System

Figure 1:
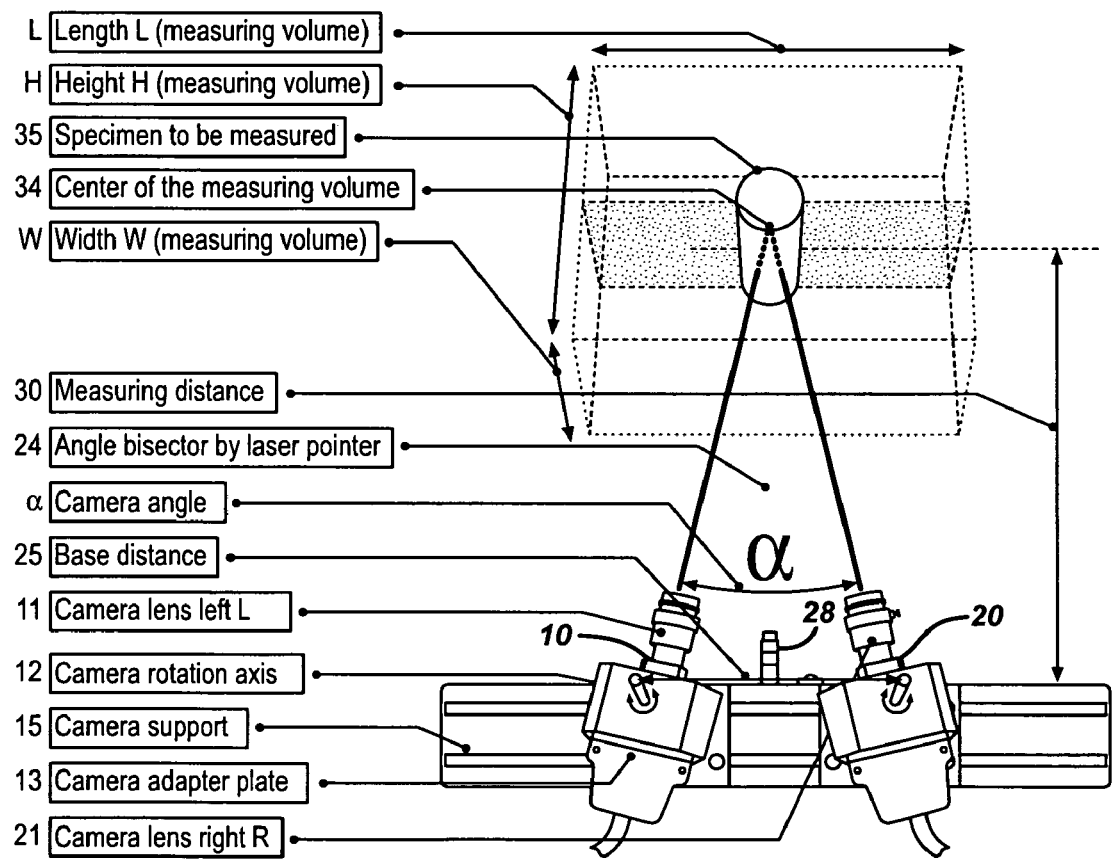
FIG. 1 shows a schematic view of a prior art image analysis system.
Figure 2:
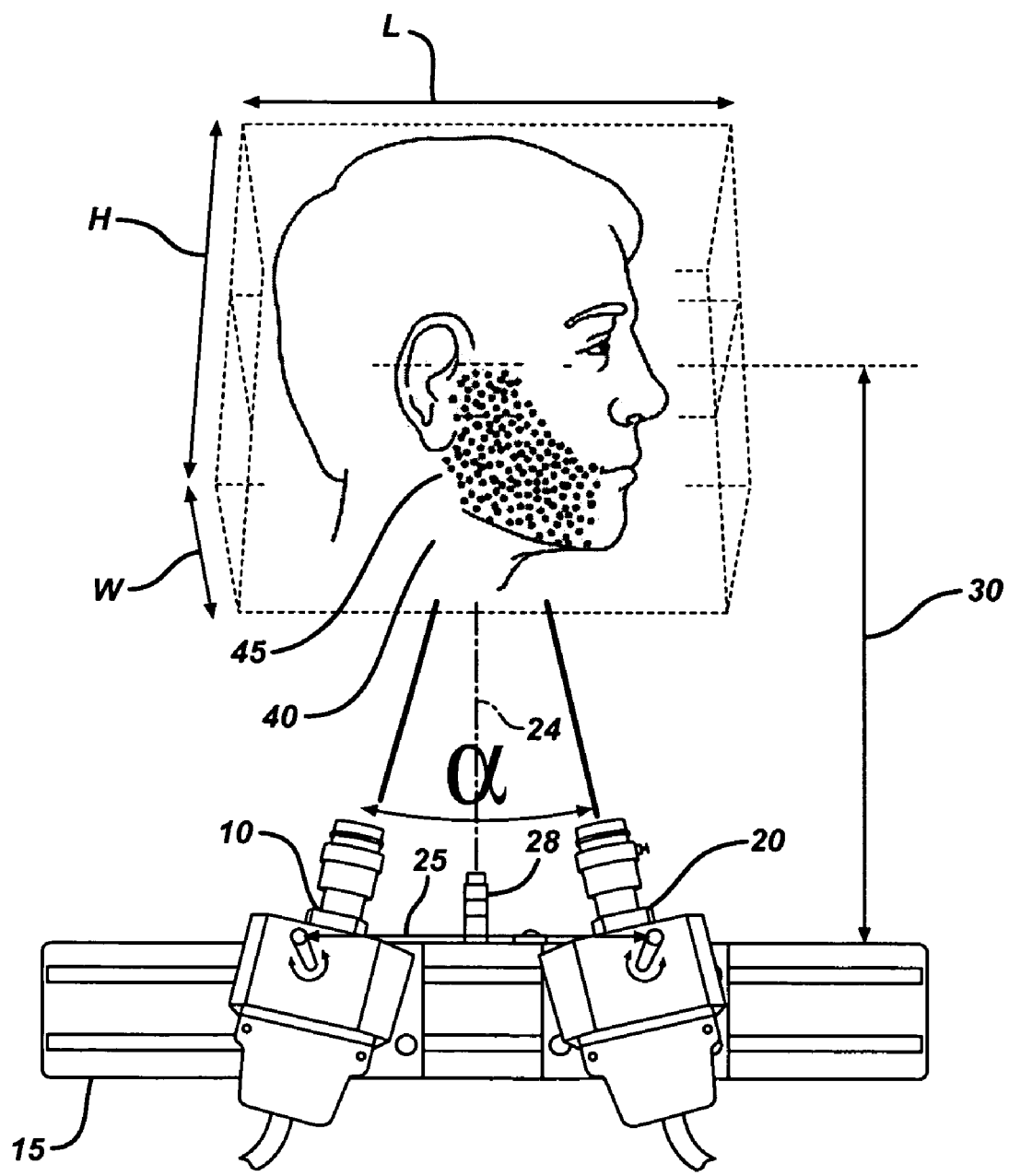
FIG. 2 shows a schematic view of an imaging system of FIG. 1 employed in a method of measuring the skin according to one embodiment of the invention.
Figure 3:
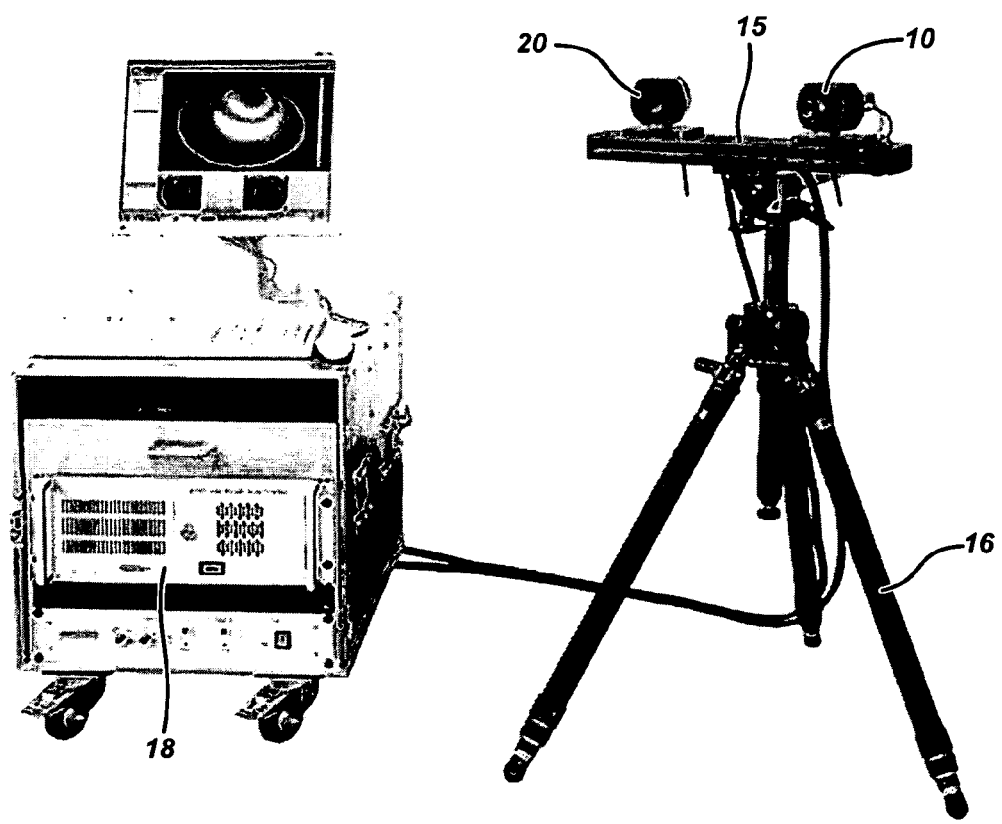
FIG. 3 shows a perspective view of the image system of FIG. 1.

Reference is made to FIGS. 1-3.

For the 3D deformation and strain measurements, sample 35 (shown schematically in FIG. 1) to which forces should be applied (which according to the invention as shown in FIG. 2 is an external skin surface of a living person 40, for example during shaving), is viewed by a pair of high resolution, digital CCD cameras 10, 20, which measure the sample's 3D coordinates and the 3D deformations. The camera pair is simply placed in front of the object being tested at a working distance 30. A typical working distance is 1 meter to 2 meters. The 3D image correlation photogrammetry technology is a combination of two-camera synchronized image correlation and photogrammetry. A regular pattern or a random pattern 45, with good contrast, is applied to the surface of the test object, such as to the surface of the skin, which deforms during the test. While a regular pattern can be used, such as an array of dots aligned in repeating columns and rows (such as a rectangular lattice), a random pattern is preferred so as to avoid a situation that could theoretically occur with a periodically repeating or regular pattern that a deformation occurs in an integer amount of the pattern, such that the camera might mistake such a deformation for a massive or rigid body translation. The random pattern does not have to be absolutely random in a strict or mathematical sense such as from a random number generator, it is sufficient that the pattern is not perceptibly a periodically repeating pattern. The deformation of this pattern under the applied load conditions (which according to an embodiment of the invention is the act of shaving) is recorded by the CCD cameras and evaluated. The initial image processing defines unique correlation areas known as macro-image facets, typically 5-25 pixels square, across the patterned imaging area. Each facet center is a measurement point that can be thought of as an extensometer point and strain rosette. These facets are tracked in each successive image with sub-pixel accuracy (to $100^{th}$ of a pixel). Then, using conventional photogrammetric principles (such as discussed in Mikhail, E., Betel, J., and McGlone, J., *Introduction to Modern Photogrammetry*, John Wiley and Sons, 2001, which is hereby incorporated in its entirety by reference), the 3D coordinates of the patterned surface of the specimen are calculated. The results are the 3D shape (contour) of the component, the 3D displacements, and the plane strain tensor of every point on the patterned surface of the object.

The 3D image correlation tracks changes in the applied micro-pattern (stochastic pattern), rather than a projected pattern, and uses ordinary white light, rather than coherent laser light. The system tracks the pattern applied to the measurement surface with sub-pixel accuracy. This means that as long as the object remains within the field of view of the cameras, all of the local deformations can be tracked. Thus, large deformations can be analyzed in a single measurement. Rigid body motion does not affect the measurements, and can also be calculated from the original pixel registration. Indeed, measurements can be continued after an object being studied has been removed, processed and replaced within the camera viewing zone.

Sensitivity with 3D image correlation is 1/30,000 the field of view. For example, with a 3 cm field of view, sensitivity is 1 micron, and with a 30 cm field of view, it is 10 microns. A field of view of several meters square is not a problem as long as deformations of several 10's of microns are present. The system intrinsically measures 3D shape, and therefore 3D deformations are measured simultaneously, rather than sequentially.

An example of a commercially widely available 3D image correlation photogrammetry digital camera system to obtain the foregoing results is the system made by the company GOM mbh ("Gesellschaft fuer Optische Messtechnik") (address: Mittelweg 7-8, D-38106 Braunschweig, Germany; website www.gom.com) marketed under the trade designation ARAMIS system and described in their publication "ARAMIS User Manual v5.4.1 (year 2005), which is hereby incorporated in its entirety by reference; this ARAMIS system is widely distributed in the United States such as by the company Trilion Quality Systems (address: Four Tower Bridge, 200 Barr Harbor Drive, Suite 400, West Conshohocken, Pa. 19428; website www.trilion.com), which is the system described in the above "Background" section in use for example in the aerospace industry, the universities and NASA, and in the technical literature therein. This system permits a large measuring area, since with the same sensor both small and large objects, such as those in size from 1 mm to 2 meters, can be measured, and strains in the range of 0.05% up to several hundred %. FIG. 1 schematically illustrates such a system.

The left camera 10 has a left camera lens 11, and the right camera 20 has a right camera lens 21. The cameras are each connected to a camera adapter plate 13 and mounted to a camera support 15 such as a rail supported by a camera tripod 16. For adjustment, the cameras can rotate their camera rotation axis 12, which are separated from each other by base distance 25. The cameras 10, 20 are located to the left and right, respectively, of angle bisector 24 generated by a laser pointer 28 that bisects the camera angle α ("alpha") at which the cameras are directed to the specimen (35, 40) to be measured. Laser pointer 28 is used only for calibration to align cameras 10, 20, it is not in use during measurement of the strain such as when the test subject is shaving.

Object 35 to be measured is located at an approximate center 34 within a measuring volume defined by a width W, height H and a length L.

In operation, the system is a non-contact optical 3D deformation measuring system, as illustrated in FIG. 1 or FIG. 2. It analyzes, calculates and documents deformations of the skin surface. The graphical representations of the measuring results provides an understanding of the behaviour of the skin surface to be measured. The system recognizes the surface structure of the object to be measured in digital camera images and allocates coordinates to the image pixels. The first coordinates are already gathered when recording the reference conditions which represents the undeformed (for example, an unstressed skin condition prior to the shaving action) state of the skin surface. After or during the deformation to the skin surface to be measured, further images are recorded. Then, the system compares the digital images and calculates the displacement and the deformation of the skin surface characteristics relative to the reference image. The system is suitable for 3D deformation measurements under static and dynamic load in order to analyze deformations and strain of real components.

A typical set-up of hardware components is illustrated in FIG. 3. A suitable arrangement of hardware and software components to operate the measurement system includes: a pair of 1.3M cameras (10, 20) with 50 mm lenses (11, 21) connected to a computer via a "Firewire" connection (Apple Computer, Inc.'s trade designation of its widely available IEEE-1394 interface, a computer and digital video serial bus interface standard); and a 64-bit dual processor computer (18) with a Linux operating system and Aramis application software version 6.0.0-4 (software is periodically updated by its manufacturer GOM mbH). The cameras are assembled and sold by the company GOM using commercially available 50 mm lenses from Schneider (Jos. Schneider Optische Werke GmbH of Bad Kreuznach, Germany), but other 50 mm lens can also be used. The designation "1.3 M" indicates a nominal 1.3 Megapixels, for example a camera resolution of 1280×1024 pixels for each image.

The typical frame rate for the camera system is 10 fps ("frames per second", referring to the still frames per second). This frame rate was determined to be adequate for all or most all of the test subjects except a test subject who shaved exceptionally fast. It is understood that typical video has a frame rate of about 30 fps, and that the designation "high-speed" can range from 480 fps to 80,000 fps. Other cameras are available for the system that are higher resolution (4M) but at a lower frame rate (max 7 fps) or a higher speed (480 fps). The frame rate as "fps" can also be expressed in terms of Hz, e.g. 12 fps=12 Hz.

To make measurements, the measuring volume is selected. For a human face 40 or leg a suitable selected volume for the camera and lens configuration used here is approximately 135 mm×108 mm×108 mm. The calibration of the system utilizes a certified calibration plate based on the selected volume. Volumes ranging from 10 $mm^3$ to 1000 $mm^3$ are possible, and are chosen depending on the size of the skin area to measure.

A suitable set of system components is shown in the table below:

| System | 1.3 M camera |
|---|---|
| Facial measuring volume with 50 mm lens | 135 mm × 108 mm × 108 mm |
| Camera resolution | 1280 × 1024 pixels |
| Camera chip | ⅔inch CCD |
| Max. frame rate | 12 fps |
| Shutter time | 0.1 ms up to 2 s |
| Strain measuring range | 0.05% up to 100% |
| Strain accuracy | up to 0.02 % |
| Displacement sensitivity | 6 microns |

Instead of the CCD cameras, it is also possible to use suitable CMOS cameras, which are believed to have similar parameters.

While the above described camera speed in the range of 10 to 12 fps preferred, the camera speed is not critical; one of skill in the art will appreciate that it is possible to use a camera speed of several thousand frames per minute, e.g. 70,000 fps, and that one simply needs enough speed to capture enough strain pictures. One of skill in the art appreciates that the practical limits of frame speed are determined by the computer memory (RAM) and the "Firewire" interface, such that the number of pixels decreases with increasing frame speed, and that the fewer pixels that are present then the lower the resolution possible.

A typical procedure for making measurements involves the following steps:

1. Applying a stochastic pattern to the surface of the skin area of interest, such as via a temporary tattoo design (described further hereinbelow);

2. capturing a reference image in the form of synchronized stereo digital images;

3. applying shaving preparation (e.g. shave cream) to the area of interest (for shaving applications). Some of the patterned dots are left free of shave prep so that the computer can relate to the reference image;

4. capturing a series of frames in the form of synchronized stereo digital images that encompass a stroking motion of the razor; and 5. analyzing the series of captured images using the evaluation mode of the Aramis system software, which recognizes the applied pattern on the reference image and subsequent strained images. The 3D coordinates, 3D displacements and the plane strain tensor are calculated using photogrammetric evaluation, and the results graphically displayed.

In order to analyze the images, the operator identifies a start point in the images. The area to be evaluated (computation mask) and the start point are defined directly in the camera images. The software then calculates square or rectangular image details or boxes, which are called facets, over the patterned area. Preferably the pattern applied to the surface being observed is smaller than the facet size. Each facet can be chosen to be made up of, for example, about 15 pixels×15 pixels. To improve resolution, the facets can have an overlap area, for example a 2 pixel overlapping area can be suitable for stationary objects such as those that are fixtured. It has been determined that for analyzing a shaving action it is suitable to chose a facet to have a 25 pixel square (25×25 pixels). It is preferred with facets of this size to use an approximate half-facet size overlap, that is a 13 pixel overlapping area. This helps with accuracy during shaving, where the test subject is moving, in order to cover more points with the facets. In the summary flowchart of FIG. 6 these steps are referenced in operation blocks 1 and 2.

Figure 4:
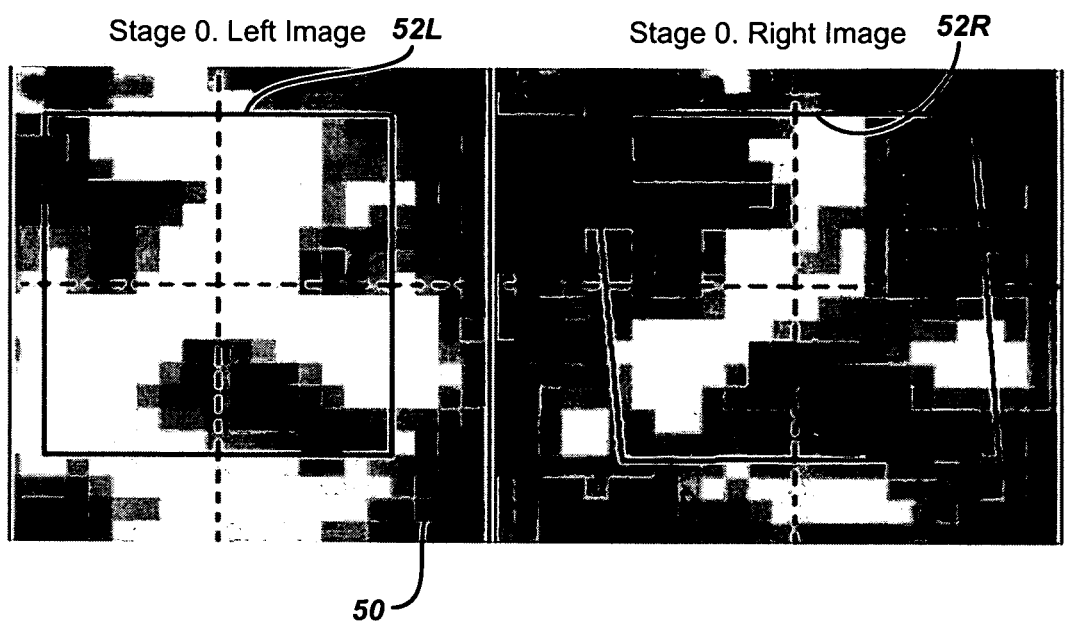
FIG. 4 shows a schematic representation of a digital optical image illustrating pixels and facets in an undeformed state.
Figure 5:
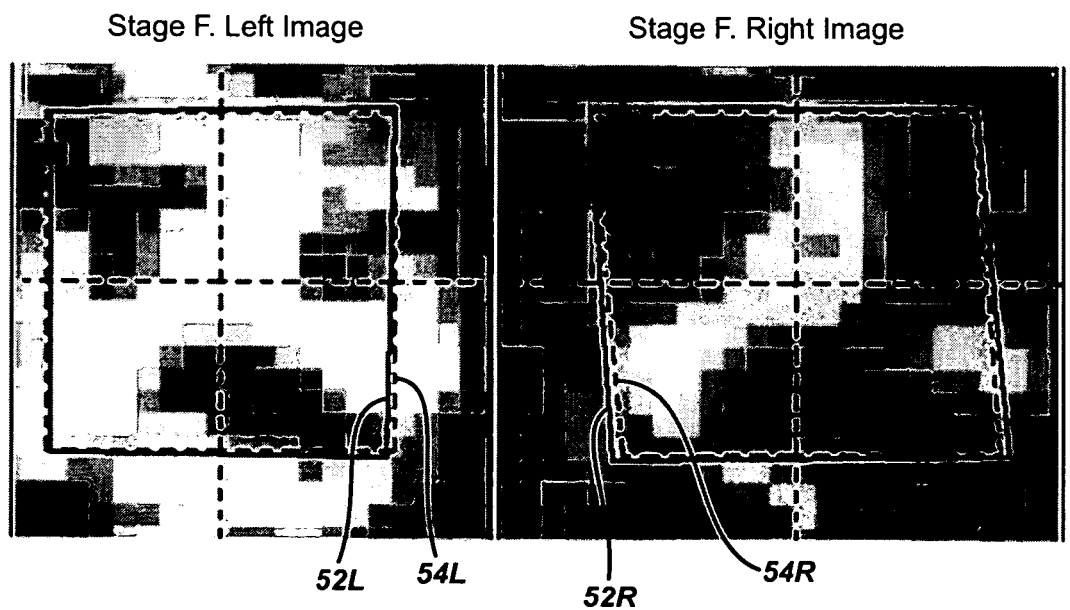
FIG. 5 shows a schematic representation of a digital optical image illustrating pixels and facets in a deformed state.

The facets will be explained with reference to FIGS. 4 and 5. FIG. 4 shows an example of pixels 50 defining rectangular-shaped facets, each pixel 50 being the smallest unit and represented as a square or box. The pixels have individual gray levels. FIG. 4 shows an exemplary pair of facets (15×15 pixels) of the left camera 10 and of the right camera 20. FIG. 4 reflects the applied pattern in an unstressed state, thus forming the image for the undeformed reference state. FIG. 5 shows an example of the facets shown in FIG. 4 having been deformed after the patterned object is taken through successive, intermediate deformation stages (not shown) to a final deformation state ("stage F"). The black quadrilateral in FIG. 4 and FIG. 5 superimposed on the pixels 50 illustrates the facet in the undeformed state. As seen in FIG. 4 in the undeformed state, the left camera 10 contributes the left image upon which facet 52L is constructed, and the right camera 20 contributes the right image upon which facet 52R is constructed. The facet from left camera 10 appears as a square, while the facet from right camera 20 appears tilted resembling a trapezoid, since, relative to the left camera 10, the right camera 20 is focused on the same region of the object, e.g. face 40, but is taking a picture at an angle α to the left camera 10.

As seen in comparison in FIG. 5, on the deformed patterned object, the facets 52L, 52R have undergone deformation and are shown in dashed lines as deformed facets 54L, 54R, respectively. For convenient comparison, the undeformed facets 52L, 52R are also shown on FIG. 5.

Figure 6:
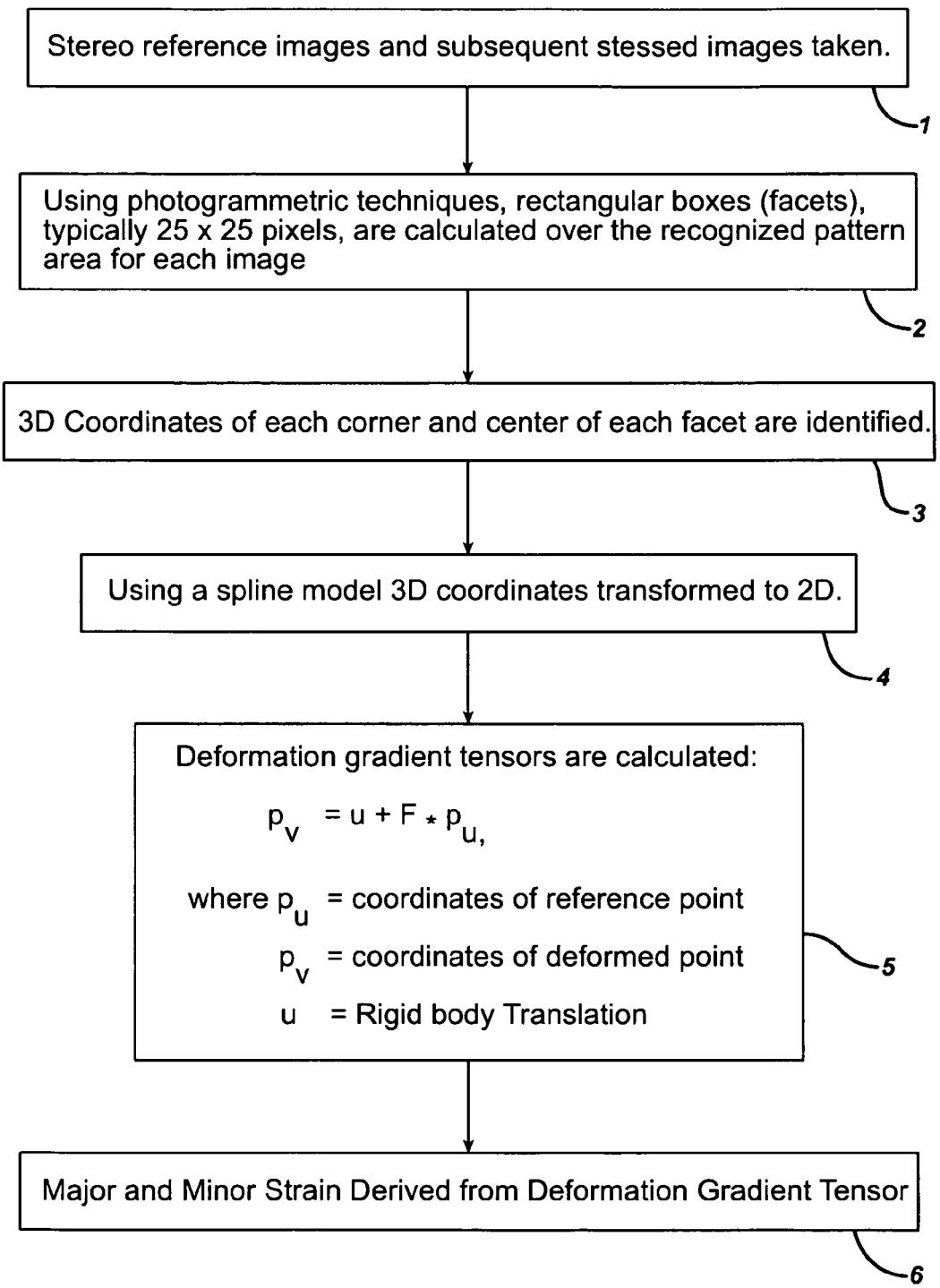
FIG. 6 shows a flowchart of optical image analysis steps.

The steps taken in the image processing in order to calculate major and minor strain are summarized in the flowchart of FIG. 6.

A reference condition is compared to a series of deformed conditions. The Aramis system software determines the 2D coordinates of the facets from the corner points of the facets and the resulting center of each facet. Using photogrammetric methods, the 2D coordinates of a facet, observed from the left camera 10, and the 2D coordinates of the same facet, observed from the right camera 20, lead to common 3D coordinates of each corner and center of each facet. (This is referenced in operational block 3 of the flowchart in FIG. 6). The change in these coordinates as the surface is strained is measured for each subsequent image pair (left-right) and the deformation relative to the reference image is calculated. The values are reported as various displacement and strain values. For the measurement of shaving it is preferred to report "major strain" as a percent change (% change). The major strain direction follows the razor as it passes over the skin so this is believed to be the most relevant parameter for studying shaving.

The facets act as virtual strain gauges. Each facet can be thought of as a virtual 3D extensometer. An array of facets acts as a virtual strain rosette; this is an approximate analogy since a strain rosette is usually considered as 2D, whereas the facets are 3D. With respect to a facet in its undeformed and deformed states, the difference in tensor length is calculated by looking at the change in length of the leg between the deformed state and the reference state, and expressed as a percent (%) change. Because the coordinates that are determined are in 3D from a curved surface, they are translated first into 2D using a transformation (such as a spline model, as referenced in operational block 4 of the flowchart in FIG. 6) and then applying engineering strain calculations. With reference again to the flowchart of FIG. 6, as shown in operational block 5, the deformation gradient tensors are calculated according to the known relation:

$$p_v = u + F \cdot p_u,$$

where
$p_u$=the coordinates of a reference point
$p_v$=the coordinates of the deformed point
u denotes rigid body translation.

As noted in operational block 6, the major and minor strains are derived from the deformation gradient tensor. The primary direction is the major strain. For background information, the basic strain relations are discussed in the Appendix at the end of this application's specification.

Because rigid body motion that is seen by both cameras is subtracted out in accordance with the above relation, then any inadvertent motion of a test subject, while shaving, for example moving his head or body within the field of view of the cameras (or even walking within the field of view), does not detract from imaging the strain in the skin due to the razor's shaving action. This analytic technique is well suited to measure strains in the skin as they occur when a person shaves himself or herself in normal use, without having to unnaturally constrain the test subject.

If a person has very coarse beard hair, that may also be recognized by the imaging system as a pattern; that is not a disadvantage since beard hair grows in an irregular pattern.

Comparing Shaving Characteristics

Figure 8:
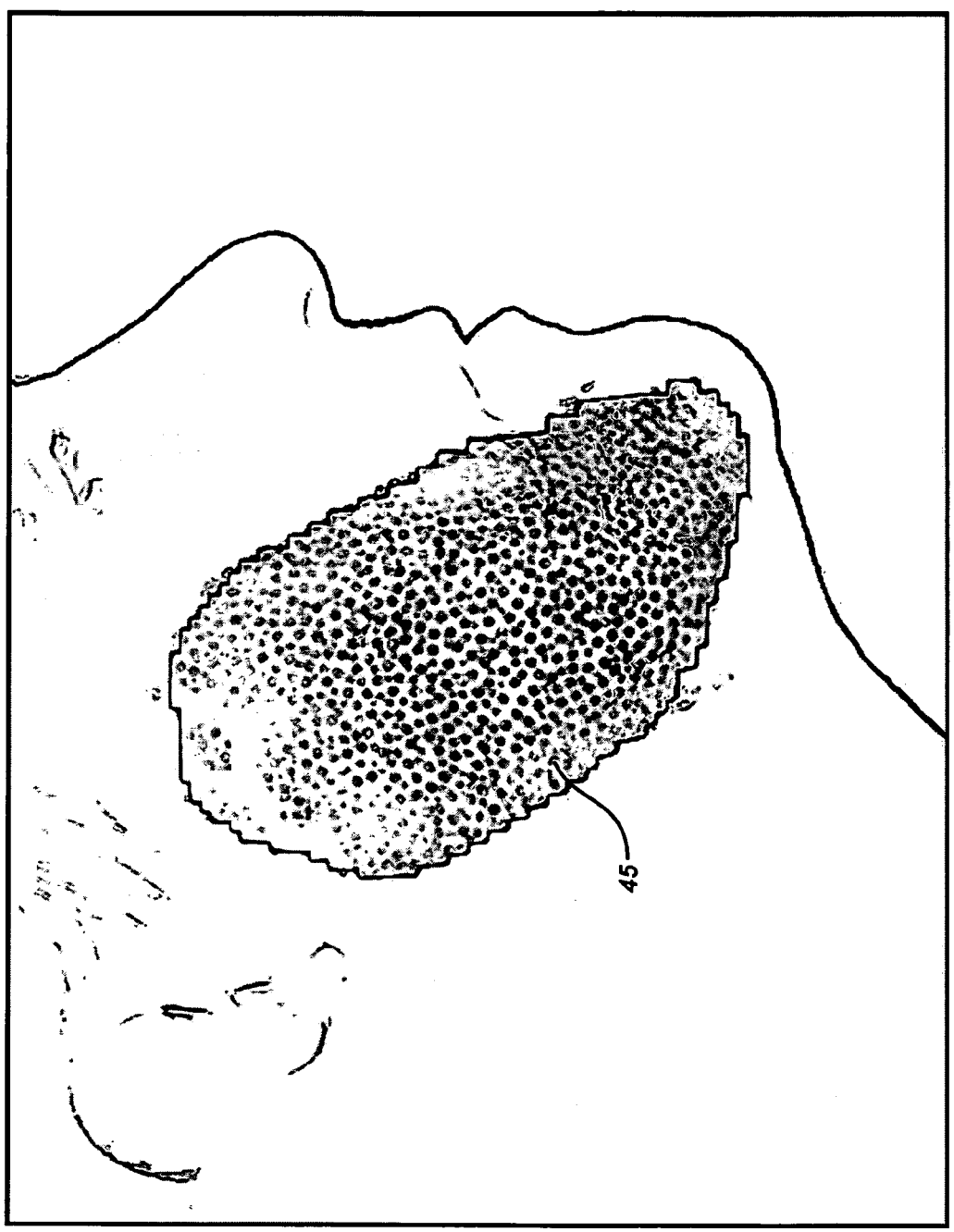
FIG. 8 shows an optical image of the reference pattern on the skin employed in a method of measuring the skin according to one embodiment of the invention.

A reference image is shown in FIG. 8, which illustrates a digital image of pattern 45 prior to shaving (the dark, somewhat jagged line bounding pattern 45 is an artifact of cropping the image to enhance visibility). The image shows a generally strain-free, unloaded condition of the shaving surface.

Figure 9:
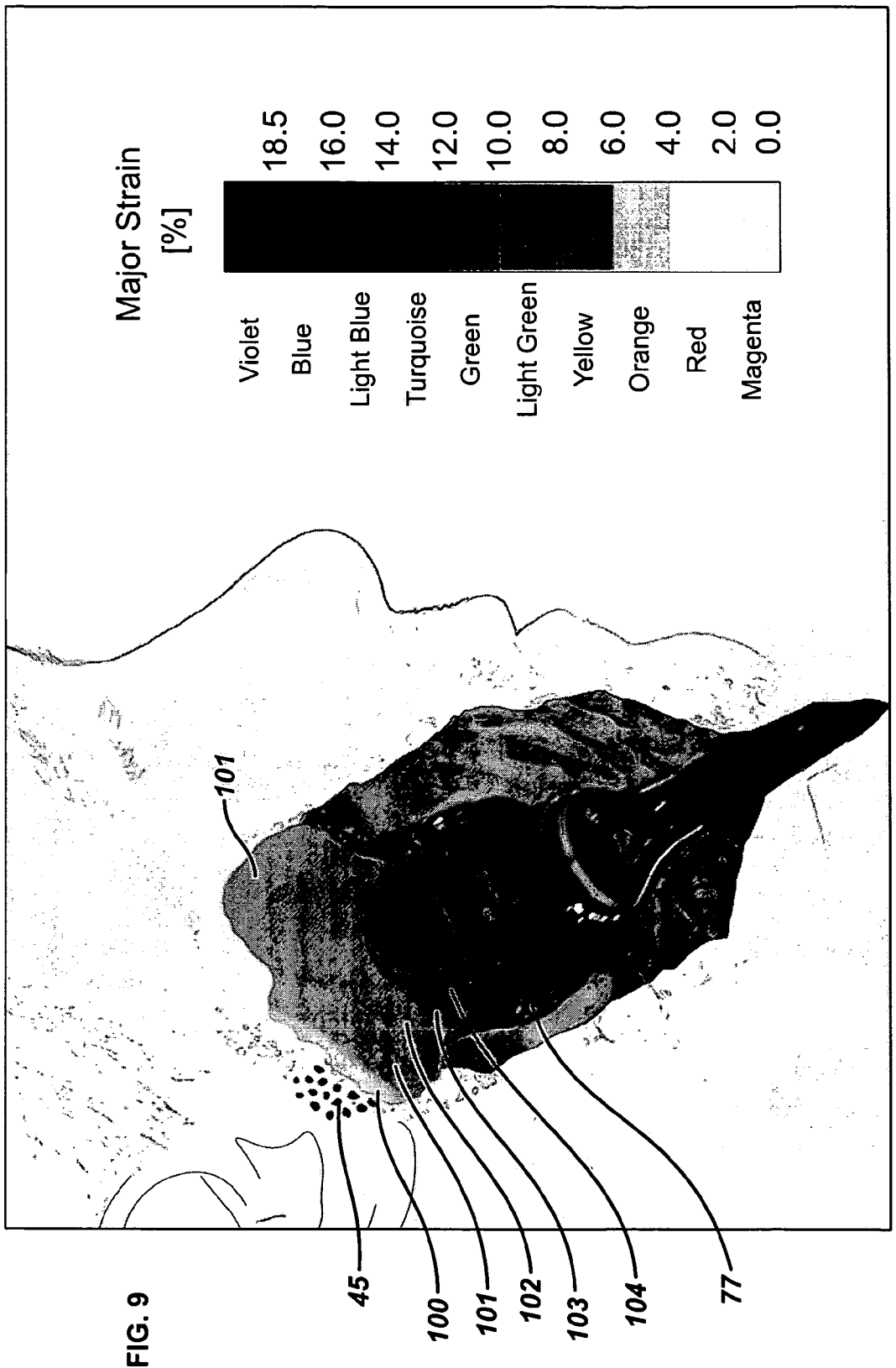
FIG. 9 shows a schematic view in grey scale of skin strain at a mid-stroke shaving position.
Figure 10:
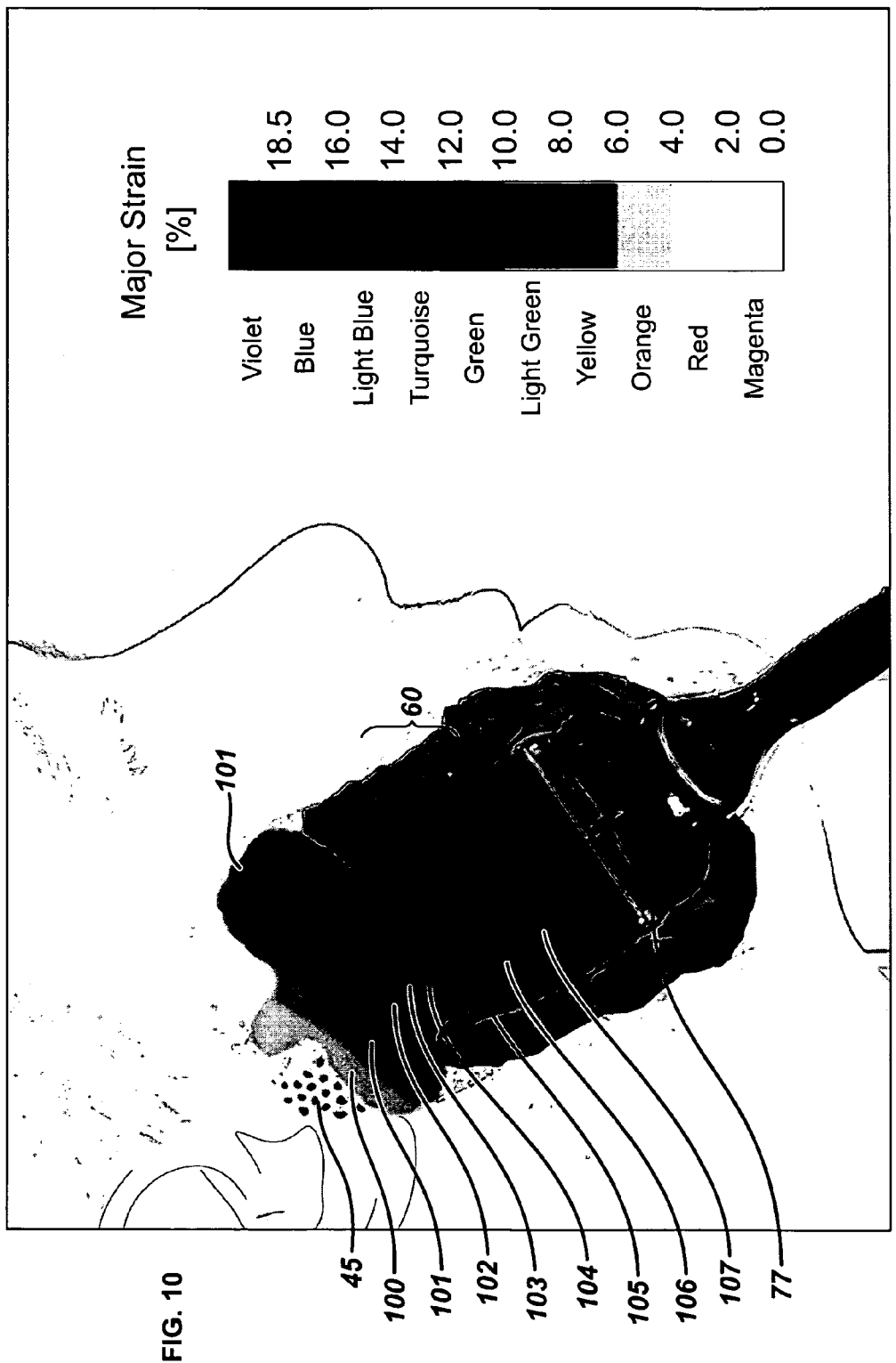
FIG. 10 shows a schematic view in grey scale of skin strain at an end-of-stroke shaving position.
Figure 11:
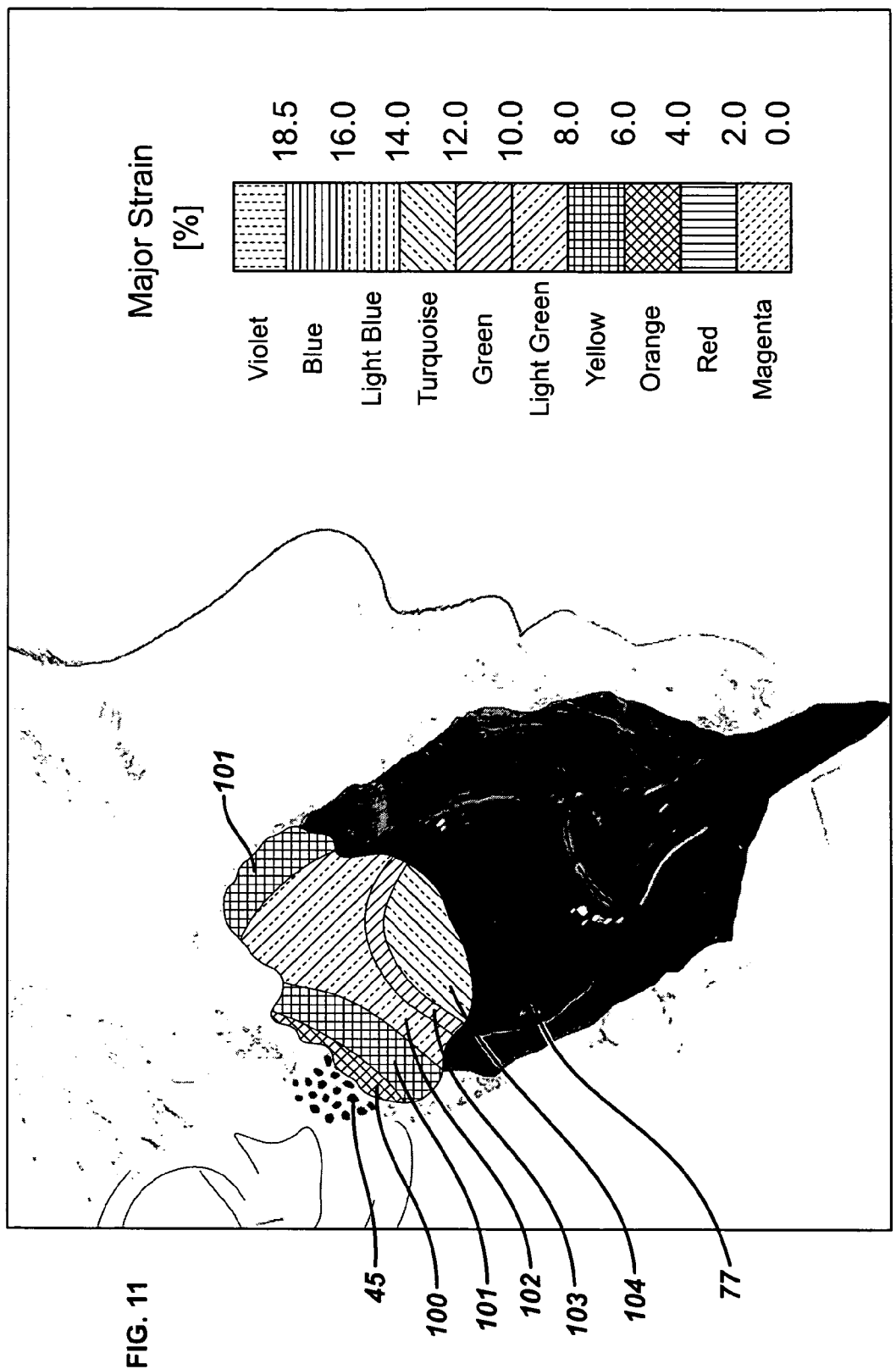
FIG. 11 shows a schematic view in cross-hatching scale of skin strain corresponding to FIG. 9.
Figure 12:
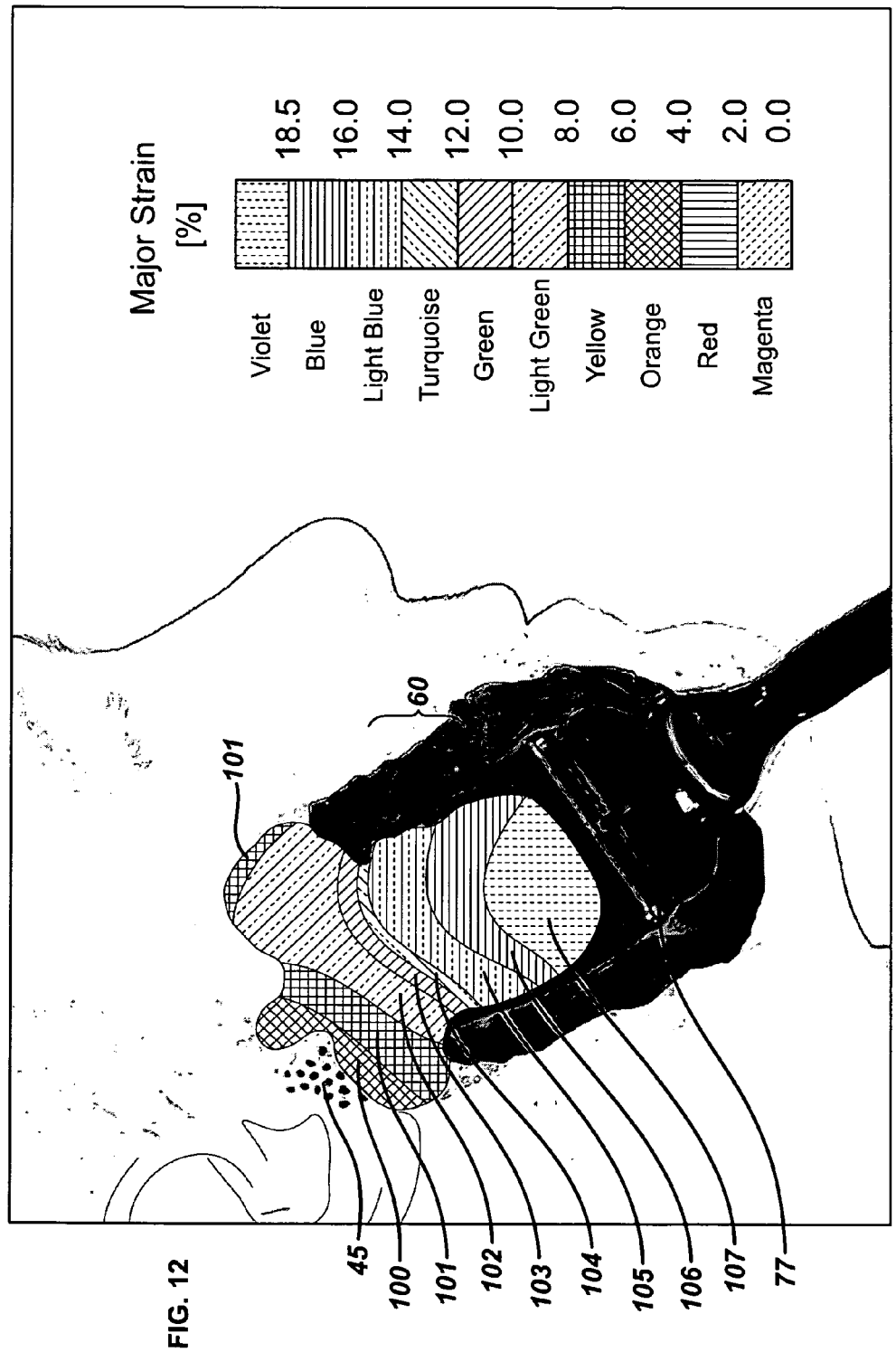
FIG. 12 shows a schematic view in cross-hatching scale of skin strain corresponding to FIG. 10.

The strain patterns on the skin being shaved are illustrated schematically in FIGS. 9-12. FIG. 11 is a cross-hatched version of the gray-scale image in FIG. 9. FIG. 12 is a cross-hatched version of the gray-scale image in FIG. 10. The strain in the areas behind the razor is represented by bands or regions of similar magnitude, as depicted by the regions of similar shading, with the scale "% Major Strain" showing the corresponding scale for the shaded region. The Aramis imaging system provides these bands in color, and they are superposed over the black dots of the reference image shown in FIG. 8; however, the strain bands are rendered herein in grey scale (and with the black reference dots removed) in FIGS. 9 and 10, and schematically in cross-hatch in FIG. 11 and FIG. 12, for convenience of photo-reproduction and printing on paper. The corresponding color is also indicated on the legends in FIGS. 9-12.

FIG. 9 shows an image of the face being shaved over skin with pattern 45 with blade unit 77 positioned at about mid-stroke. FIG. 9 shows the maximum strains present in bands (100, 101, 102, 103, 104) in the respective skin surface portions that have been shaved. In FIG. 11 the strain bands (100, 101, 102, 103, 104) are depicted using different cross-hatching to indicate the several strain levels. For example, the mesh formed by intersecting vertical and horizontal lines indicates a strain level between about 6% and 8% in band 101; on a color image available from the Aramis system that band would be indicated with e.g. a yellowish color. It will be noted that the higher strain levels are seen closer to behind the razor, such as in strain band 104. It will be appreciated that the commercially available Aramis system generates a color image in which the colored bands or regions tend to blend into one another, for example a slightly higher strain region is indicated with e.g. a light green color, and the yellowish colored lower strain region blends with a somewhat diffuse border into the next higher strain region, and there is also present the black reference dots shown in FIG. 8. Such a light green higher strain region corresponds in FIG. 11 to the cross-hatching of downwardly slanted alternating solid and dashed lines used to represent the strain band 102 between about 8% to 10%. In FIGS. 9-12 the grey scale or cross-hatching depictions schematically indicate that the various strain regions lie next to one another, and, as mentioned, the black reference dots of FIG. 8 have also been removed to facilitate clarity. As seen in FIG. 9 (or FIG. 11), there are about five (5) readily identifiable bands (100, 101, 102, 103, 104) of different strain magnitude. Each of FIGS. 9 and 11 illustrates in a region just behind the razor a strain level of between about 12% but less than 14% major strain as the highest strain band 104 on that image, indicated in FIG. 11 with the cross-hatching that is upwardly slanted alternating solid and dashed lines (to represent a turquoise color on an image from the Aramis system, as indicated on the legend).

FIG. 10 shows an image of the face being shaved over skin with pattern 45 with blade unit 77 positioned at about the end of stroke. The image of the type shown in FIG. 10 is about ten (10) images subsequent to the image of FIG. 9. As shown in FIG. 10, since the image capture is dynamic the previous strains that were present in the region depicted in FIG. 9 have decreased since the razor has moved further away from the FIG. 9 region and is not pulling it as much, since that region ("midstroke", designated approximately with bracket 60 in FIG. 10) is now further behind the razor as the razor has advanced lower on the face towards the jaw. As seen in FIG. 10, there are eight (8) readily identifiable bands (100, 101, 102, 103, 104, 105, 106, 107) of different strain magnitude. FIG. 10 illustrates a region just behind blade unit 77 of strain above 18.5% major strain in band 107. This is illustrated in FIG. 10 by bands of darker grey shading than are seen in FIG. 9. In FIG. 12 the strain band 107 corresponding to the highest strain band seen in FIG. 10 (above 18.5%) is indicated with vertical dashed lines (to represent a violet color on an image from the Aramis system).

Figure 13:
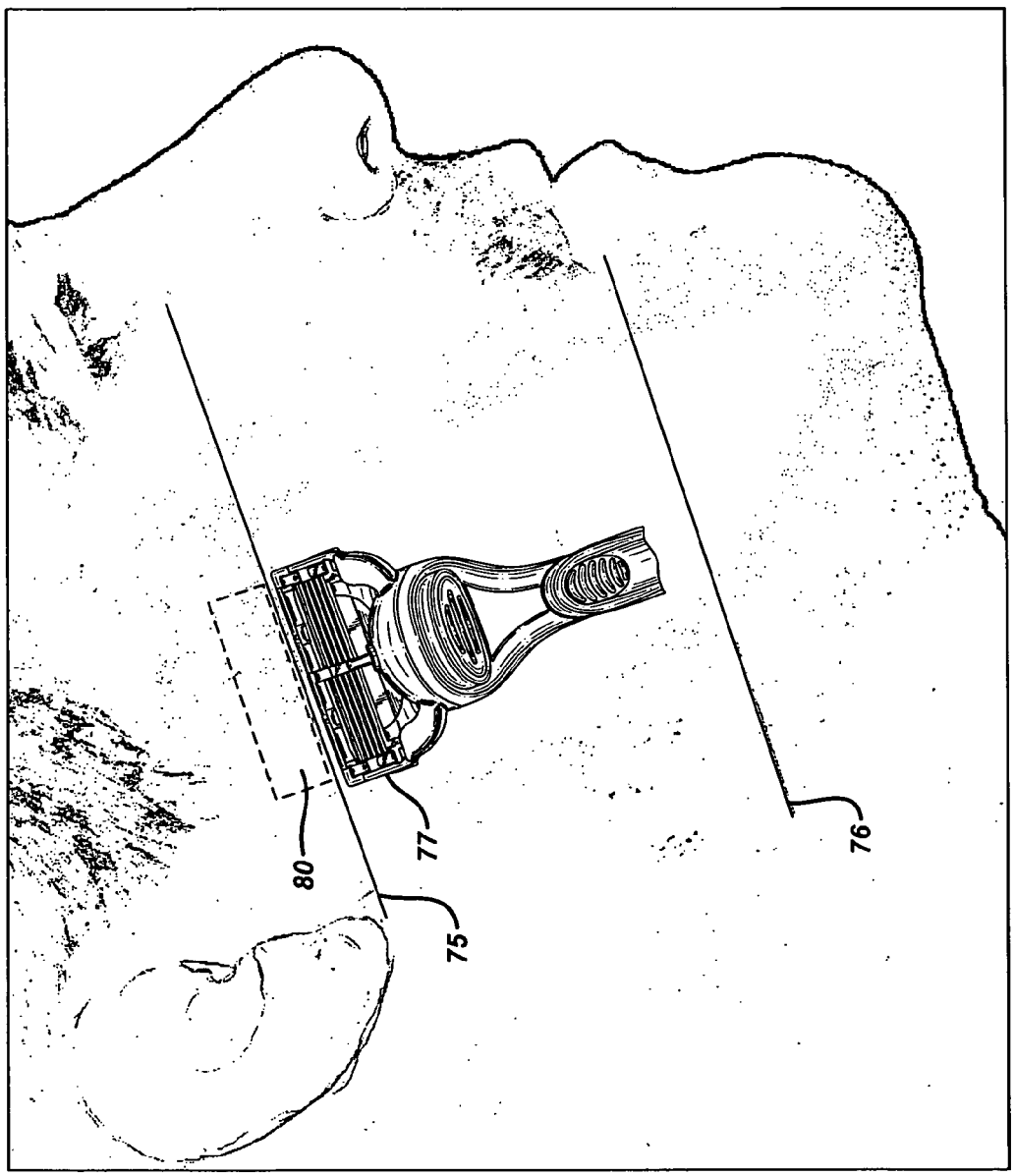
FIG. 13 shows a schematic representation of a strain measurement area near start of stroke.
Figure 14:
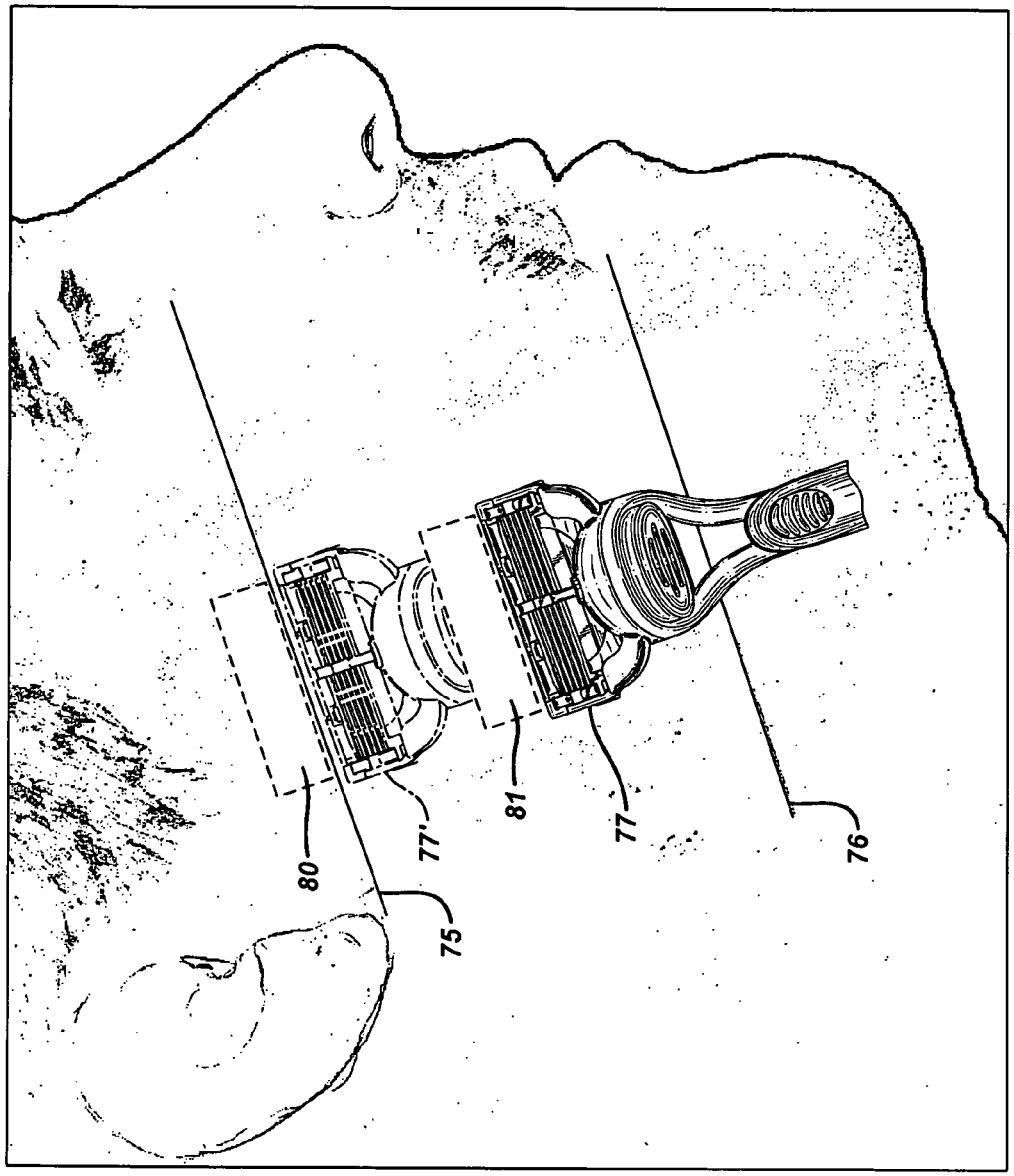
FIG. 14 shows a schematic representation of a strain measurement area near mid-stroke.
Figure 15:
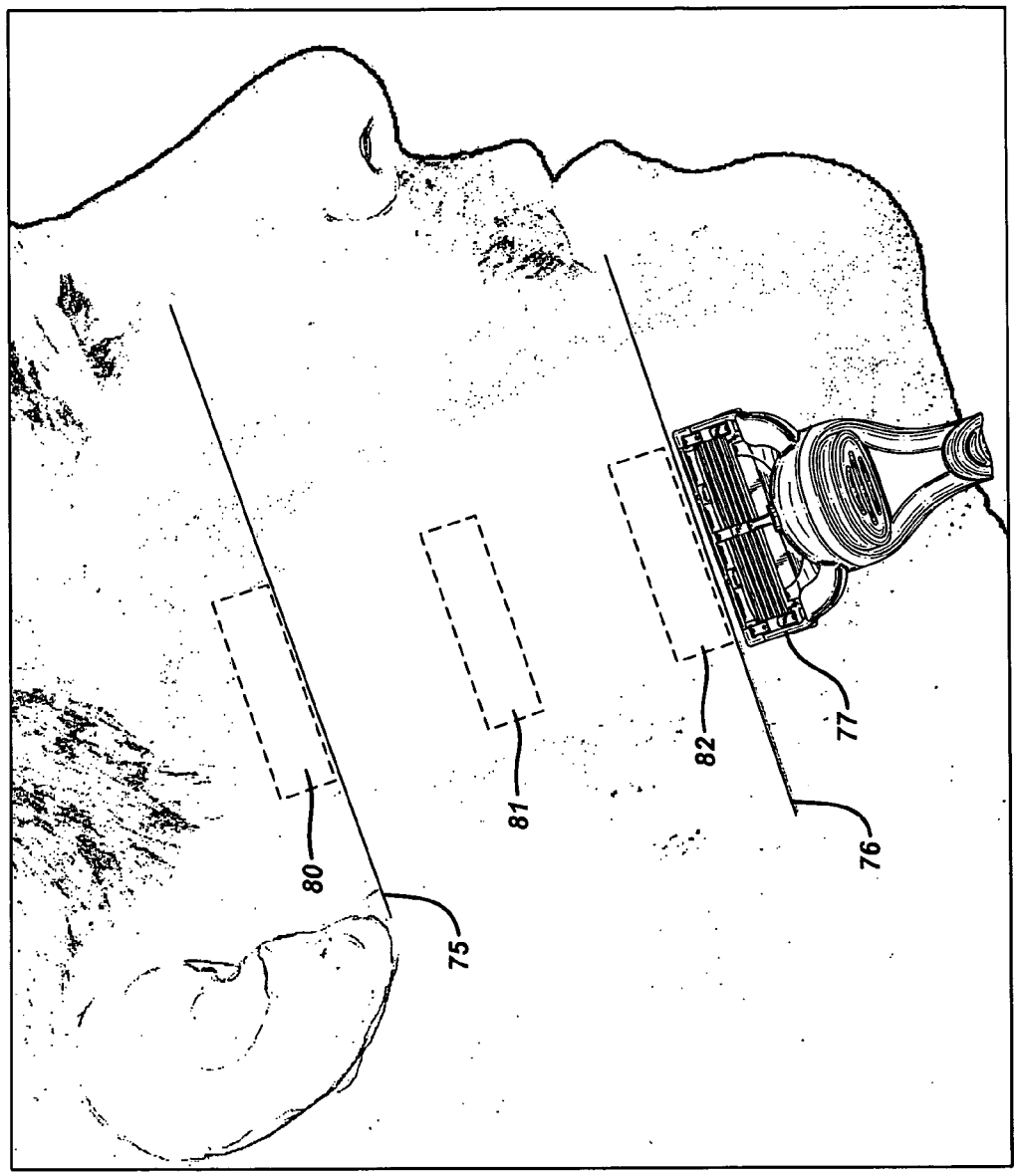
FIG. 15 shows a schematic representation of a strain measurement area near end-of stroke.

Image analysis is explained with reference to FIGS. 13-15. It is understood that the analysis depicted relative to FIGS. 13-15 is performed on the images shown in, for example FIG. 10, or equally in FIG. 12 upon completion of shave stroke. For convenience to show the technique of defining representative spatial regions, FIGS. 13-15 omit the depictions of the bands of strain and reference dot pattern 45. To analyze the images, a group of images is selected that starts just after the shave stroke has begun and ends approximately near a line extending back from the lip (with respect to images collected when shaving the face). Sometimes a pair of images, that is images from the left and right cameras 10, 20, is referred to as a "stage" or "rendered image" since it reflects a 3D rendering calculated from the left and right camera individual digital pictures, but for simplicity each "stage" is referred to as "image". Within that set of images, an area just behind the razor is selected, and the average strain in that area is recorded. The "area behind the razor" is meant in the sense that it trails the razor, in that that area has just been shaved and the razor has moved past it, exposing it to be imaged.

As shown in FIG. 13, an imaginary start line 75 is constructed from the nose to the ear. FIG. 13 depicts an approximate start-shaving position. An imaginary end line 76 is constructed approximately parallel to start line 75 extending backwards from the lip. As the razor blade unit 77 is drawn past start line 75 a first measurement area 80 is chosen on the image seen in FIG. 12. The measurement area 80 is chosen to be approximately the size of blade unit 77, and located just behind the blade unit ("behind" in the sense of being opposite the direction of razor travel during the shaving stroke). It is understood that the imaginary lines 75 and 76 and reference measurement area 80 are constructed over the strain bands image resulting for example in FIG. 11 or 12, omitted here for easier depiction. Since measurement area 80 is constructed over the strain bands in, for example, FIG. 11, the software in the Aramis system selects and averages the strains within that bounded measurement area 80 and reports the average major strain in that measurement area 80. It will be understood that within a measurement area, instead of the average strain, other parameters indicative of shaving performance could be chosen; for example, it is possible to instead calculate the minimum strain, or the maximum strain, and the standard deviation.

As shown in FIG. 14, the user has drawn the razor further down towards the jaw, and blade unit 77 is approximately at a mid-stroke position. For illustration purposes, the previous start position in FIG. 13 is indicated with a phantom-line blade unit 77'. FIG. 14 illustrates how a second measurement area 81 is chosen at this position, behind blade unit 77, within which the average strain is calculated.

As shown in FIG. 15, the user has drawn the razor further down such that blade unit 77 is approximately at an end-of-stroke position, prior to the user beginning to lift the blade unit away from the skin. A third measurement area 82 is chosen at this position, behind blade unit 77, within which the average strain is calculated. Any desired number of measurement areas can be provided between beginning of stroke and end of stroke; it is presently preferred to use four such measurement areas. The selected measurement areas can be adjacent to one another and it is also acceptable if they are slightly overlapping.

Four measurement areas selected as with the exemplary measurement areas 80, 81, 82 were selected from the set of images so as to be distributed over a reasonable amount of the distance of the entire shave stroke, and then their individual averages were averaged together. It is preferred that the four such measurement areas be distributed so as to cover the distance from a start of stroke to end of stroke over a reasonable length of stroke before the user starts to lift blade unit 77 off the skin. For example, over the overall shave stroke between start- and end-of-shave there may be between eight (8) and twenty (20) images, with twelve (12) images being common; this varies based on stroke speed. Four (4) images that encompass the strain just behind the razor over the total area were selected, approximately every third or fourth image based on 12 images overall, and corresponding measurement areas selected and their average strains calculated. It is understood that another number of measurement areas, e.g. a number more than four, could have been selected between the start and end of shave stroke.

Comparative razor testing: These images provide a quantitative tool to compare the performance characteristics of different razors. When comparing razors, one looks at the difference in average % major strain over the stroke area. It is also understood that if in the measurement areas 80, 81, instead of major strain, the maximum strain or the minimum strain or the standard deviation have been evaluated, then one would look at differences in the maximum strain or minimum strain or standard deviation. In this manner a strain exerted on the skin produced by two different razor blade units can be compared. It is also possible to evaluate differences between a test and a control blade unit that has a different feature in the blade unit, such as a different guard, or even the same blade unit mounted on different handles to test performance differences possible owing to the ergonomics of a handle. Such testing can assess differences between existing razors or facilitate developmental testing of prototype razors.

A comparison was made between two razors manufactured by the assignee of the present application, The Gillette Company, (Boston, Mass., USA), namely razors marketed to male consumers under the trade designations "Fusion" and "Fusion Power", each widely commercially available in the U.S. market since late 2005, and in other markets. Each of the "Fusion" and "Fusion Power" razors is a safety razor whose cartridge has five blades on its primary shaving surface positioned between a guard at the front and a cap at the rear. This razor cartridge is shown in assignee's U.S. Pat. No. 7,131,202 (Pennell et al.), which is hereby incorporated by reference, in particular in FIGS. 1-3 therein.

The manual "Fusion" razor is depicted for example in assignee's U.S. Design Pat. D534,313 (Provost et al.), hereby incorporated by reference, and in U.S. Pat. No. 7,131,202 at FIGS. 1-2, and is also seen in FIGS. 9-15 of the present application (without in any way limiting the generality of the measurement procedure). This version "Fusion" razor is referred to as "manual" in the sense that the motion occurs from the manual action of drawing the razor across the skin and it does not have a motor on the razor exciting additional blade motion.

The "Fusion Power" razor is depicted for example in U.S. Design Pat. D534,315 (Provost et al.) and in pending patent application U.S. Ser. No. 11/220,008 filed 6 Sep. 2005 (Schnak et al.) (to publish as US 2007/0050995 A1), which are both hereby incorporated by reference. This "Fusion Power" razor is referred to as a "power" version razor since there is a power source (e.g. a battery) as well as a motor driving an eccentric weight (also called flyweight) located in the handle that, when energized, causes during shaving use small amplitude oscillation of the razor cartridge that is connected to the handle.

A comparison was made to determine whether the "Fusion Power" razor in shaving use exhibits less drag than a "Fusion Manual" razor. Each razor was used in its normal, intended operational manner, that is, during shaving the "Fusion Power" razor was energized so that it vibrated. The major skin strain was measured on the x-, y- and z-axes. Twenty-five test panelists shaved following a 24-hour hair growth period, and the strokes were measured during shaving. Differences in major strain were determined between the two razors. For the manual "Fusion" razor the average major strain measured was about 14.3%. For the "Fusion Power" razor the average major strain measured was about 13%. This shows a difference of at least 9% lower strain when using the "Fusion Power".

Other Skin Applications

It is understood that the aforementioned analysis technique can be applied to other applications of a stressing force applied to the skin to determine a response characteristic in the skin. For example, one could measure strain on the skin as hair is being plucked out for example using an adhesive tape lifting or wax depilatory strips, as an example of testing hair epilation products.

It is theorized that a cleanser agent applied to skin dries out the skin, that the skin thereby would become stiffer or otherwise be referred to as less supple. It is thus hypothesized that, in the presence of the same force as applied to skin that has been treated with the cleanser as compared to that skin not treated with the cleanser, then in the cleanser-treated skin there will be less strain since the skin is stiffer. If a moisturizing agent is applied to make the skin softer or more supple, then in the presence of the same force such moisturizer-treated skin would yield more and show a higher strain.

Figure 16:
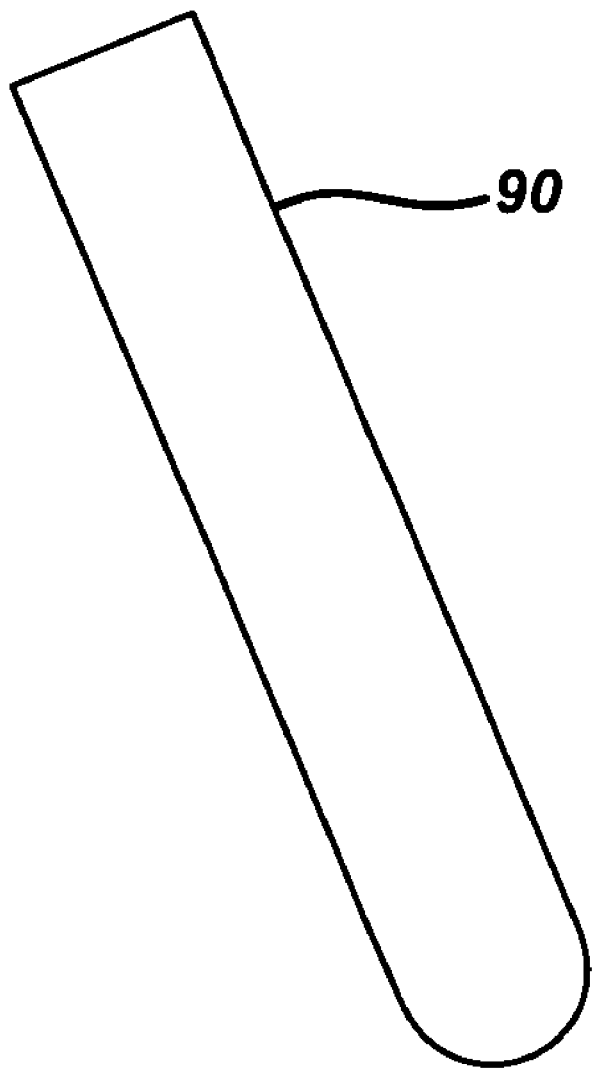
FIG. 16 shows a blunt probe employed in a method of measuring the skin according to another embodiment of the invention.

In optical image testing of the effect on the skin of a moisturizing product, such as a lotion, cream or emollient, having been applied, it is suggested that a finger of a person or as shown in FIG. 16 a blunt probe object 90 (which emulates a finger) be dragged along a portion of skin during the test in order to transmit a force to the skin. Probe 90 has a suitable radius at its tip to be generally smoothly dragged across the skin. The force applied can arise not only from an externally applied force such as a finger or probe 90, but also from internally caused forces; for example, a test subject can be asked to flex a muscle, such as smiling, frowning or making a facial expression, in order to apply a force to the skin and measure the skin deformation.

The Temporary Tattoo Pattern

One of skill in the art appreciates that for imaging the skin while shaving, the pattern should desirably not be damaged by exposure to the shaving environment, typically involving water and a shave prep such as soap or a shave cream or gel, and it is also desired that the pattern not be permanent but be generally readily removable from the skin upon the conclusion of the test. Also, in general, if the skin is exposed to a lotion such as a moisturizer as part of testing and imaging, a pattern should be applied that will not be readily smudged by the material being tested.

In order to pattern the skin surface to have a suitable target to generate the reference and deformed images, the skin of a subject was painted by hand by stippling the paint to the cheek with a narrow paint brush so as to create "dots". A water-insoluble paint was chosen such as a commercially available paint from a hardware store, for example the oil-based enamel paint sold in the United States under the trade designation "Rustoleum" in the color black. Dabbing this paint with the point of a fine-tip paint brush to the skin gave a random pattern of dots of high contrast which gave suitable results during the imaging and analysis. This method of applying the skin pattern with paint had the disadvantages, however, of a strong odor, being messy, exposing the person to excess paint, requiring careful preparation that was time-consuming, and being inconvenient to remove from the skin. While a spray paint technique could possibly be used such as a spray paint can by intermittently depressing the can's button, or using an airbrush technique, to more quickly give a suitable random pattern, in order to adequately protect a person's eyes, nose, ears, hair and clothing during such an application would require elaborate masking of those areas, and could still expose the person to excess paint spray or fumes, and would thus also be inconvenient.

Figure 7:
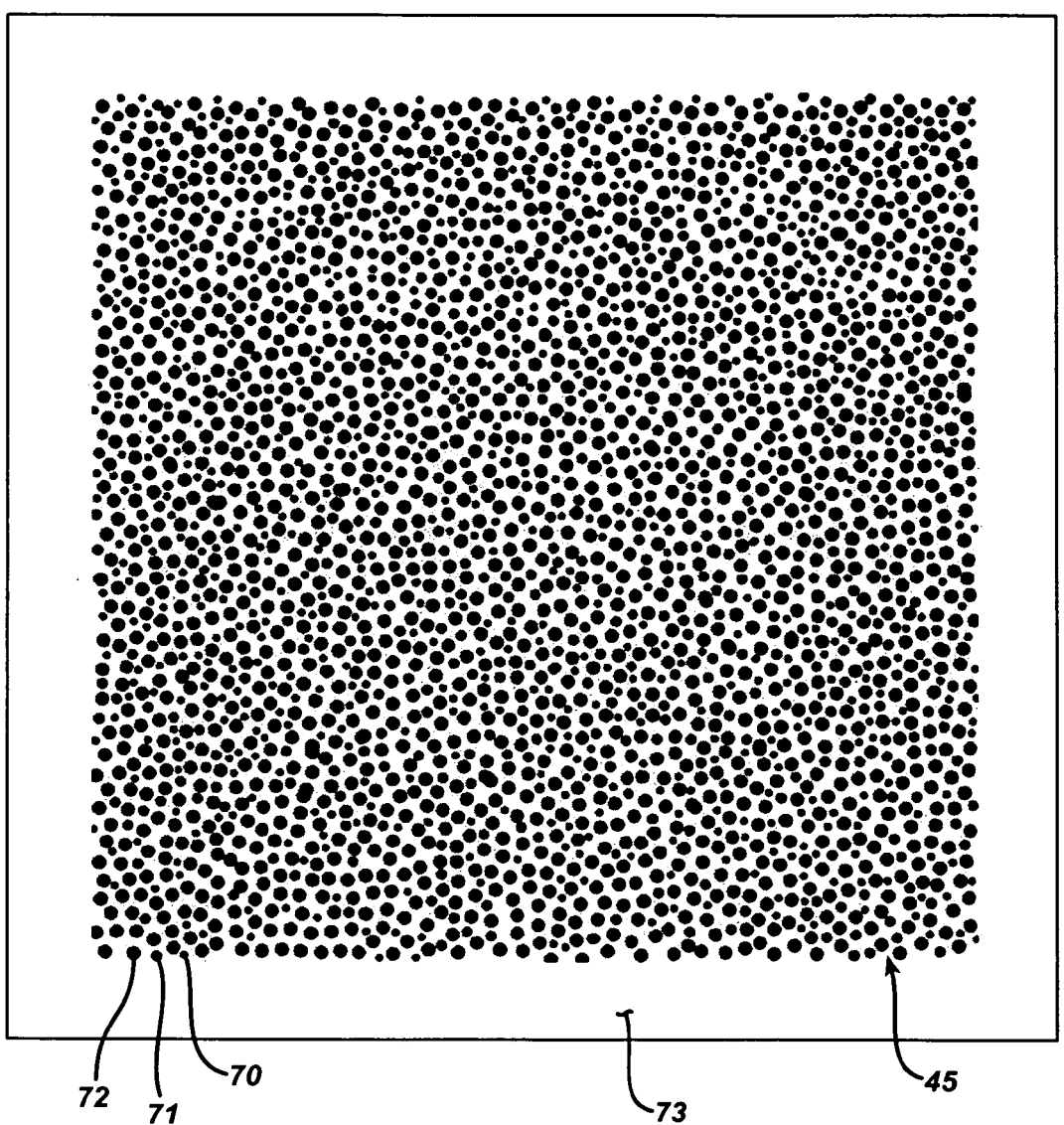
FIG. 7 shows a preferred stochastic pattern transferable to the skin for use with the method employed in FIG. 2.

In order to provide a pattern 45 that could quickly be applied to a face or body surface to be shaved and imaged, a transfer pattern was developed, as shown in FIG. 7. The pattern 45 can be prepared as a temporary body tattoo printed with standard FDA-approved ink as shown in FIG. 7 and easily transferred to the skin surface. The tattoo pattern 45 is removable or temporary, as those words are used herein, in that the pattern 45 can be wiped off or removed from the skin on which it has been applied such as by alcohol or by vigorous, normal washing with water and conventional soaps, make-up or cosmetic removal compositions (such as petroleum-based lotion), and the like. While the present temporary tattoo may be removed with repeated washings with soap and water, it is more quickly removed by use of an alcohol. The present temporary tattoo is contrasted with permanent tattoos which cannot be wiped off or removed by washing, and can only be removed by medical intervention or the like, such as by laser or surgical means.

The skin is first cleaned, for example with 70% isopropyl alcohol, and the transfer paper 73 applied to the skin area to be patterned. The transfer paper 73 is wetted with alcohol to transfer the ink pattern 45. It has been determined that the ink used is resistant to removal with water, resistant to the shave preparation used (e.g. shaving soap, foam or gel), and resistant to the act of shaving itself (e.g. the action of rubbing the cartridge over the skin or the blades moving over the skin), and yet the transferred pattern is advantageously easily removable with alcohol at the conclusion of the test.

It was found convenient to create pattern 45 shown in FIG. 7 as a computer data file using a commercially available desktop publishing software such as Adobe Photoshop. Pattern 45 has indicia distributed in a random pattern. It is preferred that the indicia be three different size dots in a generally random distribution. The diameters of the respective dots are: small dots 70 of 1.6 mm (0.063 in), medium dots 71 of 2.1 mm (0.083 in), and large dots 72 of 2.6 mm (0.103 in) diameter. It is not required that the dots be precise circles having a mathematically true diameter, the dots can be of a non-circular or arbitrary shape, such as small ovals or ellipses, or even small polygonal shapes including rectangular. The distribution of the dot sizes in the overall pattern is approximately one-third each size. The pattern 45 could be fashioned of just two different dot sizes; however, three different dot sizes is preferred. Pattern 45 can comprise more than three different dot sizes. Pattern 45 with this size distribution is small enough to allow a good raster of calculation facets during evaluation, and it also large enough to be resolved by the camera. (The image of FIG. 7 is printed out as a square of 5 inch×5 inch)

It is preferred that the density of pattern 45 be in the range of about 40% to about 60%. The lower approximate "40% density", for example, means that for a given square area of pattern 45 about 40% is occupied by the darker image (e.g. the dots, collectively) and 60% occupied by the background space. The background, in order to give sufficient contrast, is neutral or so-called "white" space. The upper approximate "60% density", for example, means that for a given square area of pattern 45 about 60% is occupied by the darker image (e.g. the dots, collectively) and 40% occupied by the neutral ("white") space. An approximate midrange value of about 50% pattern density is believed to give good results. In the preferred embodiment, pattern 45 shown in FIG. 7 was suitable in practice with a pattern density of about 42.5% (thus the remaining "white" space comprises about 57.5%). Pattern 45 is preferably of a consistent pattern density over its extent, thus facilitating applying it to the skin surface such as a cheek or leg.

The pattern 45 is printed on a substrate 73. Substrate 73 can also be referred to as a web or release web, since in the art of transfer tattoos it is known that the web releases printed pattern 45 to transfer it to the skin. Substrate 73 is preferably moisture-permeable (moisture absorbing, such as absorbing an alcohol); this assists in releasing the printed pattern when the substrate is placed against the skin and wetted with alcohol (e.g. isopropyl alcohol or denatured alcohol). Preferably substrate 73 is made of paper or cellulose material. It has been found convenient to use as substrate 73 what is referred to in the paper art as "blotting paper" or cigarette paper of the type commonly sold for rolling one's own cigarette. Other substrates could include paper such as Kraft paper, plastic, or composites thereof. The pattern 45 can be generated on substrate 73 in a long roll similar to wallpaper or gift-wrapping paper, preferably pattern 45 has a consistent pattern density over at least a length dimension of a size of a cheek, at least about 4 inches (approx. 10 cm), which facilitates application to the cheek.

The dots of pattern 45 are printed with inks. It will be appreciated that inks used are suitable for skin contact and are non-toxic such as those approved for food, drug and/or cosmetic use ("FD&C" or "D&C grade") in the United States. Such inks are mentioned in the U.S. Code of Federal Regulations at 21 C.F.R. Parts 73 and 74. These are generally food grade and/or cosmetic grade inks, being the same colorants manufactured in compliance with FDA regulated cosmetics. Suitable inks are pigmented and solvent based. The preferred ink is not water-soluble. A useful black ink is one containing iron oxide, which is a pigment. Dark ink is preferred, such as black ink referred to as D&C Black #2. Such inks are widely commercially available; one such supplier is the company Temptu at the address 26 West Seventeenth Street, New York, N.Y. 10011 (website www.temptu.com). It is preferred to use inks that are termed "certified", meaning certified not to contain toxins. A blue ink could also be used. Other dark colors or mixtures of ink could also be used. The ink is typically formed of an oil dye or a pigment in a carrier, and is soluble in lower alcohols but has very low water solubility. The ink or dye is preferably substantially insoluble in water, but is soluble in alcohol. Such an oil-based ink meets the criteria of being a temporary tattoo while being sufficiently water resistant to satisfy the objectives above to provide a pattern to the skin while withstanding the action of shaving. Many such inks are known in the medicinal and cosmetic arts as suitable for contact with human skin. Many such dyes are disclosed in U.S. Pat. No. 4,169,169 (Kitabatake), the teachings of which are incorporated herein by reference, including at column 3, lines 36 to 68 therein. An oil dye is formulated into an ink composition; in addition to the dye the ink will typically contain a binder, a solvent, a plasticizer and, optionally, other additives. The thickness of the ink layer of dots 70, 71, 72 will typically be on the order of 10 microns or less. It will be appreciated that the ink layer of pattern 45 deposited onto the skin is extremely thin, and does not affect the skin's characteristics, the shaving performance or shaving action, and does not interfere with taking the measurements.

The electronic data file containing pattern 45 can be printed using a conventional computer printer, as is widely commercially practiced, and for example available from the company Temptu of 26 West Seventeenth Street, New York, N.Y. 10011. Pattern 45 can be printed onto the substrate 73 paper with any known printing process such as offset, silk screen or gravure to form the temporary tattoo. Also, in order to print the tattoo, the digitized image or electronic file containing pattern 45 can be output from a computer to a conventional ink jet printer or laser jet printer whose ink cartridges have been loaded with D&C or FDA approved inks and printed onto a paper substrate, as is known in the art. This convenient form of printing is described generally in accordance with the portion of the teachings directed to printing onto a substrate as discussed in U.S. Pat. No. 6,042,881 (Ewan), the entire content of which is incorporated herein by reference. Other tattoo printing techniques onto a substrate are known in the art field, such as in U.S. Pat. No. 6,596,118 (Bailey), the teachings of which are incorporated herein by reference.

Since an adhesive is omitted, there is no need for a protective release sheet to cover the finished tattoo. Thus, the indicia of pattern 45 can be exposed to air during storage, and this further improves the convenience, simplicity and speed with which test subject persons can have their skin patterned since there is no protective or cover layer that needs to be removed and discarded. Furthermore, since the ink used is not water-soluble, that is a further reason that a protective release sheet is not needed.

The foregoing specification describes numerous embodiments and variations showing the wide range of possible constructions and techniques embodying the present invention. Further variants and embodiments will readily occur to those skilled in the art on the basis of the foregoing disclosure. All such embodiments and variants are to be considered as within the scope of the invention as defined by the claims.

APPENDIX

The Basics of Strain

This section explains basics of strain and strain calculation, closely following the Aramis User Guide (v5.4.1) drawing from the books (listed in the below bibliography) Hibbitt et al.; Becker et al.; Hahn; and Kopp et al.

A.1. The Term "Strain"

Strain is the measure for the deformation of a line element and can be defined as follows:

$$\lambda = \lim_{l \to 0}\left(\frac{l + \Delta l}{l}\right)$$

The stretch ratio $\lambda$ is the relative elongation of an infinitesimal line element. A strain value $\epsilon$ can be defined as the function of the stretch ratio $\lambda$:

The following known functions are frequently used strain measures:

Technical strain:

$$\epsilon^T = f(\lambda) = \lambda - 1$$

Logarithmic or natural strain:

$$\epsilon^L = \phi = f(\lambda) = \ln(\lambda)$$

Green's strain:

$$\varepsilon^G = f(\lambda) = \frac{1}{2}(\lambda^2 - 1)$$

A.2 The Deformation Gradient Tensor

The above section defined the stretch ratio in the one-dimensional case and the general description of a strain measure. This will now be extended to the two-dimensional case.

A.2.1 Deformation Gradient Tensor Definition

In order to quantitatively display the deformation of a surface element, the deformation gradient tensor F is introduced. The deformation gradient tensor transforms a line element dX into the line element dx. In both cases, the line element connects the same material coordinates. Theoretically, it is an infinitesimal line element. FIG. 17 illustrates this case.

Thus, the deformation gradient tensor is defined as:

$$dx = F \cdot dX$$

A.2.2 Decomposing the Deformation Gradient Tensor into Polar Coordinates

A disadvantage of the deformation gradient tensor is that rotation and stretch are modeled using only one matrix. This can be compensated by splitting the deformation gradient into two tensors: a purely rotational matrix and a pure stretch tensor. The matrix can be decomposed in two different ways:

Decomposition into rotation and right stretch tensor

Mathematically, the deformation gradient tensor is decomposed as follows:

$$F = R \cdot U$$

FIG. 18 illustrates this modeling.

Decomposition into left stretch tensor and rotation.

Mathematically, the deformation gradient tensor is decomposed as follows:

$$F = V \cdot R$$

A.2.3 Major and Minor Strain Derived from the Deformation Gradient Tensor

Values $\epsilon_x$, $\epsilon_y$ and $\epsilon_{xy} = \frac{1}{2}\gamma_{xy}$ can directly be read from the stretch tensor U. It has the following form:

$$U = \begin{pmatrix} U_{11} & U_{12} \\ U_{21} & U_{22} \end{pmatrix} = \begin{pmatrix} 1+\varepsilon_x & \varepsilon_{xy} \\ \varepsilon_{xy} & 1+\varepsilon_y \end{pmatrix}$$

The strain measures $\epsilon_x$ and $\epsilon_y$ have the disadvantage of being defined as dependent on the coordinate system. This disadvantage can be eliminated by calculating major and minor strain. The symmetrical matrix U can be transformed to the main diagonal form. The two eigenvalues $\lambda_1$ and $\lambda_2$ can be calculated as follows:

$$\lambda_{1,2} = 1 + \frac{\varepsilon_x + \varepsilon_y}{2} \pm \sqrt{\left(\frac{\varepsilon_x + \varepsilon_y}{2}\right)^2 - (\varepsilon_x \cdot \varepsilon_y - \varepsilon_{xy}^2)}$$

Depending on the choice of the strain measure, the stretch ratios $\lambda_1$ and $\lambda_2$ can be transformed into corresponding strain values. The larger eigenvalue is called major strain $^1\epsilon_1$ and the smaller eigenvalue is the minor strain $^2\epsilon_2$. The corresponding eigenvectors determine the two directions of major and minor strain. The strain values thus determined are independent of the coordinate system and are universally applicable.

If the material thickness with respect to the entire surface is small, it is frequently necessary to deduce the remaining material thickness from the deformation of the surface. As the optical measuring techniques used cannot obtain any data in this dimension, the third principle strain $\epsilon_3$ can be calculated from major and minor strain $\epsilon_1$ and $\epsilon_2$, assuming a constant volume. Without determining a strain value, the relationship between the stretch ratios can be expressed more generally. The volume constancy can be defined as follows:

$$\lambda_1 \cdot \lambda_2 \cdot \lambda_3 = 1$$

Frequently, the effective strains are needed. The effective strains according to von Mises and von Tresca are available. The effective strain according to von Mises results from the following formula:

$$\varphi_V = \sqrt{\frac{2}{3}(\varphi_1^2 + \varphi_2^2 + \varphi_3^2)}$$

The effective strain according to von Tresca results from the following formula:

$$\phi_V = |\phi|_{max}$$

A.3 Calculation of the Deformation Gradient Tensor from a 2D Displacement Field The deformation gradient tensor F is calculated from a given 2D displacement field of points. For this purpose, the 2D coordinates of each point must be known both in its undeformed and in its deformed state. The definition of the deformation gradient tensor F explains how an undeformed line element is transformed into a deformed line element. In order to calculate the deformation gradient tensor for a point, a number of points in the neighborhood of the observed point is needed. For this model of calculation, a homogeneous state of strain is assumed for this set of adjacent points.

The deformation gradient tensor creates a functional connection of the coordinates of the deformed points $P_{v,i}$ with the coordinates of the undeformed points $P_{u,i}$ (i being the index for the different points). The functional connection is as follows:

$$p_v = u + F \cdot p_u$$

with:

$p_u$ Coordinates of the undeformed point
$p_v$ Coordinates of the deformed point
u Rigid body translation
Reference is made to FIG. 19.

This formula describes a linear system of equations whose unknowns are the four parameters of the deformation gradient tensor F. The deformation gradient tensor F can be interpreted as an affine transformation which transforms a unit square into a parallelogram. This system of equations can be analytically calculated for three points. If more than three points are chosen, the result is an overdetermined system of equations which generally is contradictory. In this case, methods must be used which permit a calculation with more than three points. Thus, the Gaussian least squares adjustment is used.

The number of neighboring points can be adjusted to calculate the deformation gradient tensor for one point. This thus sets the length over which the differentiation is made. The neighborhood for a point is arranged quadratically. The smallest neighborhood is a 3×3 environment which can be increased by an increment of two. FIG. 20 shows a 3×3 neighborhood.

For an even higher resolution, the deformation gradient tensor can be calculated for a four-sided facet. A facet consists of four points. The calculated deformation gradient tensor is calculated for the virtual center of gravity S. FIG. 21 schematically illustrates a four-sided facet.

This model of calculation assumes that the pure rigid body displacement, which the individual line elements received in addition to their deformation, cannot be modeled by the deformation gradient tensor F as well. This means that for the calculation of the deformation gradient tensor F all points of a neighborhood may undergo a translation. This translation may be different for the undeformed and the deformed state. The translation is chosen such that the point for which the deformation gradient tensor is being calculated is shifted into the origin.

A.4 Calculation of the Deformation Gradient Tensor from a 3D Displacement Field

The description so far dealt in detail with the calculation of strain in 2D. However, the measuring data consist of three-dimensional Cartesian coordinates of the specimen's surface. In order to be able to use the above models of calculation, the 3D data has to be transformed into the 2D space.

A.4.1 The Tangential Model

The first model assumes that the local neighborhood of a point can be well approximated by a tangential plane. Due to the arbitrary deformation of the surface, the tangential plane needs to be calculated separately for the deformed and undeformed state. The points in the local neighborhood are then projected perpendicularly onto the tangential plane. The result is two sets of points, for the deformed and undeformed state, in the two-dimensional space in which the strain now can be calculated. Summarized, this process consists of the following tasks:

Calculation of the tangential plane
Transformation of the 3D neighborhoods into the tangential planes
Coordinate transformation of the tangential plane into the 2D space
Calculation of the deformation gradient tensor from the 2D sets of points A.4.2 The Spline Model The tangential model described above provides good results as long as the assumption of the linearization of a local neighborhood of points is valid. In deep drawing, the deformed materials are mostly continuously curved planes. The problem then is to apply the characteristics to be measured to the respective object in such a frequency that the assumption of local linearity is still given. However, this characteristic can hardly be provided in reality. Therefore, it is better to use other models which are more accurate in modeling the true shape of the surface. Splines are a good model for continuously curved lines.

In order to calculate the side length not only according to a linear model, it is necessary to have more information than two points on a side. This means that the adjacent points of a four-sided facet have to be included in the calculations. FIG. 22 shows the adjacent points of the cross-hatched four-sided facet.

In the facet, the side lengths are calculated using the formed splines. The resulting lengths can be used to construct a quadrangle in the two-dimensional space. Then the strain calculations described above can be used.

A.5 Bibliography for Strain Theory

1) Aramis User Manual v5.4.1 (GOM mbH) at pp. 129-135.
2) Hibbitt, Karlsson and Lorensen, Inc. *ABAQUS—Theory Manual*, 5.7 ed.
3) Becker und Burger. *Kontinuumsmechanik*. ["Continuum Mechanics"] Teubner-Verlag, 1975.
4) Malvern. *Introduction to the Mechanics of a Continuous Medium*. Prentice-Hall, 1969.
5) Hahn. *Elastizitatstheorie*. Teubner-Verlag, 1984.
6) Kopp und Wiegels. *Einfuhrung in die Umformtechnik*. ["Introduction to Transformation Technique"] Verlag der Augustinus Buchhandlung, 1998.

The following reference numbers listed below are used in the specification:

| Ref. No. | Meaning |
| --- | --- |
| L | Length |
| H | Height |
| W | Width |
| α | camera angle (alpha) |
| 1 | operational block |
| 2 | operational block |
| 3 | operational block |
| 4 | operational block |
| 5 | operational block |
| 6 | operational block |
| 10 | Camera, left |
| 11 | Camera lens, left |
| 12 | Camera rotation axis |
| 13 | camera adapter plate |
| 15 | camera support |
| 16 | tripod |
| 18 | computer |
| 20 | Camera, right |
| 21 | Camera lens, right |
| 24 | angle bisector by laser pointer |
| 25 | base distance |
| 28 | laser pointer |
| 30 | measuring distance |
| 34 | center of measuring volume |
| 35 | specimen to measure |
| 40 | face of person |
| 45 | pattern |
| 50 | pixel |
| 52L | initial facet, left camera |
| 52R | initial facet, right camera |
| 54L | deformed facet, left camera |
| 54R | deformed facet, right camera |
| 60 | midstroke region |
| 70 | small dot |
| 71 | intermediate dot |
| 72 | large dot |
| 73 | transfer paper |
| 75 | imaginary nose-ear line |
| 76 | imaginary lip line |
| 77 | blade unit |
| 77' | displaced blade unit |
| 80 | measurement area |
| 81 | measurement area |
| 82 | measurement area |
| 90 | blunt probe |
| 100 | strain band |
| 101 | strain band |
| 102 | strain band |

-continued

| Ref. No. | Meaning |
|---|---|
| 103 | strain band |
| 104 | strain band |
| 105 | strain band |
| 106 | strain band |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of measuring a parameter indicative of deformation of a skin surface of a living person resulting from an applied force to said skin surface, comprising the steps of
    providing a first digital camera and a second digital camera,
    providing a pattern on said skin surface of a person to produce a patterned skin surface,
    capturing first data output from said first and second digital cameras indicative of a reference position of the patterned skin surface,
    storing said first data as reference position data,
    applying a force to said patterned skin surface,
    capturing second data output from said first and second digital cameras indicative of said patterned skin surface during the applying of force to said patterned skin surface,
    storing said second data as applied force position data,
    processing said applied force position data and said reference position data to determine movement of said patterned skin surface relative to said reference position.

2. The method of claim 1, wherein said step of applying a force to said patterned skin comprises the step of shaving said patterned skin surface.

3. The method of claim 2, wherein said step of shaving comprises shaving with a safety razor having one or more sharp blades.

4. The method of claim 2, wherein said step of detecting movement of said patterned skin surface relative to said reference position comprises determining a first set of quantitative parameter data in the skin surface during use of a first shaving implement,
    wherein said step of shaving is repeated with a second shaving implement whereupon said step of detecting movement of said patterned skin surface relative to said reference position comprises determining a second set of quantitative parameter data in the skin surface during use of said second shaving implement, and
    comprising the further step of comparing said first set of quantitative parameter data and said second set of quantitative parameter data.

5. The method of claim 4, wherein said first and second quantitative parameter data is strain data.

6. The method of claim 1, further comprising the step of moistening said patterned skin surface, and said step of applying force comprises applying force to said moistened patterned skin surface.

7. The method of claim 3, further comprising the step of moistening said patterned skin surface and said step of shaving comprises shaving said moistened patterned skin surface.

8. The method of claim 1, wherein said processing step of determining movement of said patterned skin surface relative to said reference position comprises determining a quantitative parameter.

9. The method of claim 8, wherein said processing step determines a strain in said patterned skin surface.

10. The method of claim 9, wherein said step of determining strain in the skin surface comprises determining a plurality of strain data corresponding to a plurality of regions of skin.

11. The method of claim 10, wherein said step of determining strain in the skin surface comprises averaging said plurality of strain data.

12. The method of claim 1, wherein said step of providing a pattern comprises providing a random pattern on said skin surface.

13. The method of claim 1, wherein said step of providing a pattern comprises providing a regular pattern on said skin surface.

14. The method of claim 1, wherein at least one of said first and second digital cameras is a CCD camera.

15. The method of claim 14, wherein said first and second digital cameras are CCD cameras.

16. The method of claim 1, wherein at least one of said first and second digital cameras is a CMOS camera.

17. The method of claim 16, wherein said first and second digital cameras are CMOS cameras.

18. The method of claim 1, wherein said step of applying a force to said patterned skin comprises the step of drawing a finger across said patterned skin surface.

19. The method of claim 1, wherein said step of applying a force to said patterned skin comprises the step of drawing a probe across said patterned skin surface.

20. The method of claim 1, wherein said step of applying a force to said patterned skin comprises said person flexing a muscle in order to deform said patterned skin surface.

* * * * *